US008901129B2

(12) United States Patent
Saarma et al.

(10) Patent No.: US 8,901,129 B2
(45) Date of Patent: Dec. 2, 2014

(54) METHODS OF FACILITATING NEURAL CELL SURVIVAL USING GDNF FAMILY LIGAND (GFL) MIMETICS OR RET SIGNALING PATHWAY ACTIVATORS

(75) Inventors: Mart Saarma, Helsinki (FI); Mati Karelson, Vahi (EE); Maxim Bespalov, Helsinki (FI); Mehis Pilv, Tallinn (EE)

(73) Assignee: GeneCode AS, Tallinn (EE)

( * ) Notice: Subject to any disclaimer, the term of this patent is extended or adjusted under 35 U.S.C. 154(b) by 26 days.

(21) Appl. No.: 13/514,906

(22) PCT Filed: Dec. 13, 2010

(86) PCT No.: PCT/EP2010/069535
§ 371 (c)(1),
(2), (4) Date: Oct. 22, 2012

(87) PCT Pub. No.: WO2011/070177
PCT Pub. Date: Jun. 16, 2011

(65) Prior Publication Data
US 2013/0030180 A1   Jan. 31, 2013

Related U.S. Application Data

(60) Provisional application No. 61/285,858, filed on Dec. 11, 2009.

(51) Int. Cl.
*A61K 31/496* (2006.01)
*C07D 241/04* (2006.01)
*C07D 295/192* (2006.01)
*C07D 215/46* (2006.01)
*C07D 285/135* (2006.01)
*C07D 513/10* (2006.01)
*C07D 219/10* (2006.01)
*C07D 263/57* (2006.01)

(52) U.S. Cl.
CPC .......... *C07D 215/46* (2013.01); *C07D 295/192* (2013.01); *C07D 285/135* (2013.01); *C07D 513/10* (2013.01); *C07D 219/10* (2013.01); *C07D 263/57* (2013.01)
USPC ............ 514/252.12; 514/253.01; 514/253.13; 544/386

(58) Field of Classification Search
CPC ............. C07D 295/192; C07D 241/04; A61K 31/4965; A61K 31/496
USPC ...................................... 544/386; 514/255.01
See application file for complete search history.

(56) References Cited

U.S. PATENT DOCUMENTS

| 2,531,011 A | 11/1950 | Surrey |
| 3,232,945 A | 2/1966 | Sigal et al. |
| 3,458,525 A | 7/1969 | Wolf et al. |
| 4,426,330 A | 1/1984 | Sears |
| 4,534,899 A | 8/1985 | Sears |
| 4,902,505 A | 2/1990 | Pardridge et al. |
| 4,933,324 A | 6/1990 | Shashoua |
| 5,013,556 A | 5/1991 | Woodle et al. |
| 5,019,400 A | 5/1991 | Gombotz et al. |
| 5,108,921 A | 4/1992 | Low et al. |
| 5,109,921 A | 5/1992 | Aracena |
| 5,112,596 A | 5/1992 | Malfroy-Camine |
| 5,112,863 A | 5/1992 | Hashimoto et al. |
| 5,154,924 A | 10/1992 | Friden |
| 5,182,107 A | 1/1993 | Friden |
| 5,213,804 A | 5/1993 | Martin et al. |
| 5,227,170 A | 7/1993 | Sullivan |
| 5,260,308 A | 11/1993 | Poduslo et al. |
| 5,264,221 A | 11/1993 | Tagawa et al. |
| 5,268,164 A | 12/1993 | Kozarich et al. |
| 5,271,961 A | 12/1993 | Mathiowitz et al. |
| 5,284,876 A | 2/1994 | Shashoua et al. |
| 5,354,844 A | 10/1994 | Beug et al. |
| 5,356,633 A | 10/1994 | Woodle et al. |
| 5,395,619 A | 3/1995 | Zalipsky et al. |
| 5,413,797 A | 5/1995 | Khan et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,512,295 A | 4/1996 | Kornberg et al. |
| 5,521,291 A | 5/1996 | Curiel et al. |
| 5,527,528 A | 6/1996 | Allen et al. |

(Continued)

FOREIGN PATENT DOCUMENTS

EP  0268871 A1  6/1988
EP  0411534 A2  2/1991

(Continued)

OTHER PUBLICATIONS

Sariola, 2003, Journal of Cell Science, vol. 116, p. 3855-3862.*
Abramochkin et al., Synthesis of n-substituted 4-amino-2,3-pentamethylenequinolines, Pharm. Chem. J., 4(7):372-4 (1970).
Airaksinen et al., The GDNF family: signalling, biological functions and therapeutic value, Nat. Rev. Neurosci., 3(5):383-94 (2002).
Alonso et al., Donepezil-tacrine hybrid related derivatives as new dual binding site inhibitors of AChE, Bioorg. Medicinal Chem., 13:6588-97 (2005).
Baloh et al., Functional mapping of receptor specificity domains of glial cell line-derived neurotrophic factor (GDNF) family ligands and production of GFRalpha1 RET-specific agonists, J. Biol. Chem., 275(5):3412-20 (2000).
Bespalov et al., GDNF family receptor complexes are emerging drug targets, Trends in Pharmacol. Sci., 28(2): 68-74 (2007).

(Continued)

*Primary Examiner* — Rebecca Anderson
*Assistant Examiner* — Karen Cheng
(74) *Attorney, Agent, or Firm* — Marshall, Gerstein & Borun LLP

(57) ABSTRACT

Disclosed are compounds and methods for treating neurological and other disorders by administering to a subject in need thereof an effective amount of a compound having binding and/or modulation specificity for GFRα receptor molecules, which can be mimetics of glial-derived neurotrophic factor (GDNF) family ligands (GFLs), GFRα/RET signaling pathway agonists, and/or direct RET agonists (activators).

9 Claims, 9 Drawing Sheets

(56) References Cited

U.S. PATENT DOCUMENTS

| | | | |
|---|---|---|---|
| 5,534,259 | A | 7/1996 | Zalipsky et al. |
| 5,543,152 | A | 8/1996 | Webb et al. |
| 5,543,158 | A | 8/1996 | Gref et al. |
| 5,547,932 | A | 8/1996 | Curiel et al. |
| 5,556,948 | A | 9/1996 | Tagawa et al. |
| 5,580,575 | A | 12/1996 | Unger et al. |
| 5,583,020 | A | 12/1996 | Sullivan |
| 5,591,721 | A | 1/1997 | Agrawal et al. |
| 5,595,756 | A | 1/1997 | Bally et al. |
| 6,235,769 | B1 | 5/2001 | Clary |
| 6,287,860 | B1 | 9/2001 | Monia et al. |
| 6,887,906 | B1 | 5/2005 | Teng et al. |
| 2003/0027780 | A1 | 2/2003 | Hardee et al. |
| 2004/0034019 | A1 | 2/2004 | Tomlinson et al. |
| 2004/0142997 | A1 | 7/2004 | Chen et al. |
| 2005/0282780 | A1 | 12/2005 | Labaudiniere |
| 2007/0060526 | A1 | 3/2007 | Longo et al. |
| 2008/0176308 | A1 | 7/2008 | Ip et al. |
| 2008/0234267 | A1 | 9/2008 | Lackey |
| 2009/0203735 | A1 | 8/2009 | Corfas et al. |

FOREIGN PATENT DOCUMENTS

| | | |
|---|---|---|
| EP | 0427636 A2 | 5/1991 |
| WO | WO-88/07851 A1 | 10/1988 |
| WO | WO-88/07852 A1 | 10/1988 |
| WO | WO-89/07938 A1 | 9/1989 |
| WO | WO-91/04014 A1 | 4/1991 |
| WO | WO-93/10819 A1 | 6/1993 |
| WO | WO-94/02178 A1 | 2/1994 |
| WO | WO-95/02421 A1 | 1/1995 |
| WO | WO-01/64645 A2 | 9/2001 |
| WO | WO-2004/004660 A2 | 1/2004 |
| WO | WO-2006/094237 A2 | 9/2006 |
| WO | WO-2006/094843 A1 | 9/2006 |
| WO | WO-2006/130493 A2 | 12/2006 |
| WO | WO-2008/010984 A2 | 1/2008 |
| WO | WO-2009/024611 A2 | 2/2009 |
| WO | WO-2009/148659 A2 | 12/2009 |

OTHER PUBLICATIONS

Bindra et al., Synthesis, pharmacological activities & physicochemical properties of 4-(substituted amino/N4-arylpiperazinyl/aminocarbonyl)-2, 3-polymethylenequinolines, Ind. J. Chem., 26B:318-29 (1987).
Cope et al., Synthesis and SAR study of acridine, 2-methylquinoline and 2-phenylquinazoline analogues as anti-prion agents, Eur. J. Med. Chem., 41(10):1124-43 (2006).
Database Accession No. 1008228-16-7 (Mar. 16, 2008).
Database Accession Nos. RN: 924577-01-5, 924539-62-8, 924551-57-5, 924564-95-4, 924576-91-0, 924553-86-6, 924537-98-4 (Mar. 2, 2007).
Database Accession Nos. 00174789656, 0010560146, 0011264857, 0009961513, 0014083641, 0009749723, 0016006950, 0010558361, 0009557186, 0011975036, 0012387641, 0009828212, 0010568933, 0012521524, 0015757439 (Jan. 4, 2011).
De Souza et al., Synthesis and in vitro antitubercular activity of a series of quinoline derivatives, Bioorg. Med. Chem., 17(4):1474-80 (2009).
Doucet-Personeni et al., A structure-based design approach to the development of novel, reversible AChE inhibitors, J. Med. Chem., 44:3203-15 (2001).
Enslen et al., Regulation of mitogen-activated protein kinases by a calcium/calmodulin-dependent protein kinase cascade, Proc. Natl. Acad. Sci. USA, 93(20):10803-8 (1996).
Garces et al., Responsiveness to neurturin of subpopulations of embryonic rat spinal motoneuron does not correlate with expression of GFR alpha 1 or GFR alpha 2, Dev. Dyn., 220(3):189-97 (2001).
Gardell et al., Multiple actions of systemic artemin in experimental neuropathy, Nat. Med., 9(11):1383-9 (2003).
Gill et al., Direct brain infusion of glial cell line-derived neurotrophic factor in Parkinson disease, Nat. Med., 9(5):589-95 (2003).
Girgis et al., Phosphorous pentoxide in organic synthesis; XVII. A new synthesis of 4-arylamino-2,3-polymethylenequinolines, Synthesis, pp. 547-548 (1985).
He et al., Glial cell line-derived neurotrophic factor mediates the desirable actions of the anti-addiction drug ibogaine against alcohol consumption, J. Neurosci., 25(3):619-28 (2005).
Henderson et al., GDNF: a potent survival factor for motoneurons present in peripheral nerve and muscle, Science, 266(5187):1062-4 (1994).
International Preliminary Report on Patentability for corresponding international application No. PCT/EP2010/069535, completion date May 2, 2012.
International Search Report and Written Opinion for corresponding international application No. PCT/EP2010/069535, mailing date Jul. 8, 2011.
Jurvansuu et al., Recent inventions on receptor tyrosine kinase RET modulation, Recent Patents on Biotechnology, 2:47-54 (2008).
Knowles et al., Structure and chemical inhibition of the RET tyrosine kinase domain, J. Biol. Chem., 281(44):33577-87 (2006).
Leppanen et al., The structure of GFRalpha1 domain 3 reveals new insights into GDNF binding and RET activation, EMBO J., 23(7):1452-62 (2004).
Lin et al., GDNF: a glial cell line-derived neurotrophic factor for midbrain dopaminergic neurons, Science, 260(5111):1130-2 (1993).
Lindholm et al., Novel neurotrophic factor CDNF protects and rescues midbrain dopamine neurons in vivo, Nature, 448(7149):73-7 (2007).
Marks et al., Safety and tolerability of intraputaminal delivery of CERE-120 (adeno-associated virus serotype 2-neurturin) to patients with idiopathic Parkinson's disease: an open-label, phase I trial, Lancet Neurol., 7(5):400-8 (2008).
McKenna et al., Novel tacrine analogues for potential use against Alzheimer's Disease: potent and selective acetylcholinesterase inhibitors and 5-HT uptake inhibitors, J. Med. Chem., 40:3518-23 (1997).
Meng et al., Promotion of seminomatous tumors by targeted overexpression of glial cell line-derived neurotrophic factor in mouse testis, Cancer Res., 61(8):3267-71 (2001).
Meng et al., Regulation of cell fate decision of undifferentiated spermatogonia by GDNF, Science, 287(5457):1489-93 (2000).
Messer et al., Role for GDNF in biochemical and behavioral adaptations to drugs of abuse, Neuron, 26(1):247-57 (2000).
Mijatovic et al., Constitutive Ret activity in knock-in multiple endocrine neoplasia type B mice induces profound elevation of brain dopamine concentration via enhanced synthesis and increases the number of TH-positive cells in the substantia nigra, J. Neurosci., 27(18):4799-809 (2007).
Nunes et al., Transthyretin knockout mice display decreased susceptibility to AMPA-induced neurodegeneration, Neurochem. Intl., 55:454-7 (2009).
Parkash et al., The structure of the glial cell line-derived neurotrophic factor-coreceptor complex: insights into RET signaling and heparin binding, J. Biol. Chem., 283(50):35164-72 (2008).
Pichel et al., Defects in enteric innervation and kidney development in mice lacking GDNF, Nature, 382(6586):73-6 (1996).
Pinard et al., 4-aminoquinolines as a novel class of NR1/2B subtype selective NMDA receptor antagonists, Bioorg. Medicinal Chem. Lett., 12:2615-9 (2002).
Recanatini et al., SAR of 9-amino-1,2,3,4-tetrahydroacridine-based acetylcholinesterase inhibitors: synthesis, enzyme inhibitory activity, QSAR, and structure-based CoMFA of tacrine analogues, J. Med. Chem., 43:2007-18 (2000).
Runeberg-Roos et al., RET(MEN 2B) is active in the endoplasmic reticulum before reaching the cell surface, Oncogene, 26(57):7909-15 (2007).
Santoro et al., Minireview: RET: normal and abnormal functions, Endocrinology, 145(12):5448-51 (2004).
Sariola et al., Novel functions and signalling pathways for GDNF, J. Cell Sci., 116(Pt. 19):3855-62 (2003).

(56) References Cited

OTHER PUBLICATIONS

Shepard et al., Nuclear substituted 9-(4'-diethylamino-1'-methylbutylamino)-acridines, J. Am. Chem. Soc., 70(5):1979-80 (1948).
Singh et al., Antimalarials. 7-Chloro-4-(substituted amino)quinolines, J. Med. Chem., 14(4):283-6 (1971).
Steinberg et al., A hydrophobic binding site in acetylcholinesterase, J. Med. Chem., 18(1):1056-61 (1975).
STN Database Accession No. RN: 924811-53-0, 924789-13-09, 924762-99-2, 624759-42-2, 924756-06-9, 924740-23-8, 924730-35-8 (Mar. 5, 2007).
Tokugawa et al., XIB4035, a novel nonpeptidyl small molecule agonist for GFRα-1, Neurochem. Int., 42:81-6 (2003).
Tomac et al., Effects of cerebral ischemia in mice deficient in Persephin, Proc. Natl. Acad. Sci. USA, 99(14):9521-6 (2002).
Tomosaka et al., Enhancement of mutagenic activity of 9-aminoacridine by introducing a nitro group into the molecule, Biosci. Biotech. Biochem., 58(8):1420-3 (1994).
Tomosaka et al., The effects of substituents introduced into 0-aminoacridine on frameshift mutagenicity and DNA binding affinity, Biosci. Biotech. Biochem., 71(7):1121-5 (1997).
Vennerstrom et al., Bisquinolines. 1. N,N-bis(7-chloroquinolin-4-yl)alkanediamines with potential against chloroquine-resistant malaria, J. Med. Chem., 35(11):2129-34 (1992).
Wang et al., Persistent restoration of sensory function by immediate or delayed systemic artemin after dorsal root injury, Nat. Neurosci., 11(4):488-96 (2008).
Wang et al., Structure of artemin complexed with its receptor GFRalpha3: convergent recognition of glial cell line-derived neurotrophic factors, Strucutre, 14(6):1083-92 (2006).

* cited by examiner

METHODS OF FACILITATING NEURAL CELL SURVIVAL USING GDNF FAMILY LIGAND (GFL) MIMETICS OR RET SIGNALING PATHWAY ACTIVATORS

CROSS-REFERENCE TO RELATED APPLICATIONS

This is the U.S. national phase of International Application No. PCT/EP2010/069535, filed Dec. 13, 2010, which claims the benefit of U.S. Provisional Patent Application Ser. No. 61/285,858, filed Dec. 11, 2009, the entire disclosures of which are hereby incorporated herein by reference.

BACKGROUND

Many neurological and all neurodegenerative diseases are caused by death of neurons or loss of their neuritis. Currently, there are no drugs that are neuroprotective or neurorestorative. Several proteins supporting neuronal survival have been shown to be effective against neurological and neurodegenerative diseases in animal models and in clinical trials, e.g., GDNF family of ligands (GLFs) in Parkinson's disease and chronic pain. However, proteins are large molecules with poor pharmacokinetic properties and are cannot penetrate the blood-brain barrier.

Neurons, as non-dividing cells, require constant survival signals from neighboring cells, from the extracellular matrix (ECM) and from the environment, to remain alive. The "stay alive" signals are usually carried by neurotrophic factors promoting neuronal survival. In certain pathological conditions, such as Parkinson's (PD) and Alzheimer's diseases, neurons progressively degenerate. Neurons loose synaptic contacts, undergo axonal degeneration, and eventually die.

Currently available therapies for neurodegenerative diseases are symptomatic, and there are no other available treatments that can reverse or significantly slow down the neurodegeneration. The neurotrophic factor-based therapies hold a great promise, because in addition to the promotion of neuronal survival they also induce axonal regeneration, support the formation of synapses and stimulate functional properties of neurons.

Glial cell line-derived neurotrophic factor (GDNF) is a distant member of the transforming growth factor β superfamily and a founding member of the GDNF family ligands (GFL). This family consists of four members: GDNF, neurturin (NRTN), artemin (ARTN) and persephin (PSPN) (FIG. 1), all of which are potent neurotrophic factors (Airaksinen and Saarma, 2002). Since its discovery in 1993, GDNF has attracted substantial attention for its ability to support the survival of dopaminergic neurons, induce axonal sprouting and regulate functional dopamine metabolism in these neurons, which degenerate in PD (Lin et al., 1993). In addition, GDNF is one of the few growth factors that not only protects, but also repairs dopamine neurons in animal models of PD (Bespalov and Saarma, 2007; Lindholm et al., 2007).

Although GDNF has already shown protective and neurorestorative effects in a number of animal models of Parkinson's disease and demonstrated very promising results in two clinical trials (Gill et al., 2003; Slevin et al., 2005), a recent study failed to show clear clinical benefits of GDNF (Lang et al., 2006). This discrepancy might be explained by differences in trial setups, disease state of the patients and the properties of E. coli expressed GDNF. To date, there is no clear understanding why these three trials resulted in different outcomes.

GDNF may also be important for the treatment of amyotrophic lateral sclerosis (ALS) as GDNF is supportive for motoneurons (Henderson et al., 1994). For the treatment of depression as RET signaling increases amount of dopamine in the brain (Mijatovic et al., 2007). GDNF or its mimetics could also be used as male contraceptives (Meng et al., 2000).

NRTN is a very promising molecule as recent Phase II clinical trials with intraputamenal injections of adenovirus bearing NRTN gene demonstrated a significant improvement in Parkinson's disease patients (Ceregene Inc., press release). ARTN is being tested for neuropathy in Phase I trials conducted by Biogen Idec/NsGene as it was demonstrated to be efficient in animal model of chronic pain (Gardell et al., 2003) and being restorative for sensory neurons (Wang et al., 2008). PSPN is considered for the treatment of stroke and Alzheimer's disease (Golden et al., 2003; Tomac et al., 2002)

While the GFLs-receptor complex is considered as an adequate drug target, the GFLs polypeptides are probably the inappropriate pharmacological agents. One hurdle in protein-based therapies is bioavailability. GDNF is a basic protein of 134 amino acids, which is unable to penetrate the blood-brain barrier. Therefore, brain surgery is required to deliver it. Furthermore, GDNF, NRTN and ARTN interact with heparan sulfates—the components of the extracellular matrix (ECM) (Lin et al., 1993). This interaction dramatically reduces the diffusion of GFLs from the area of its application or production. Recombinant GDNF may induce inflammation and formation of anti-GDNF antibodies (Lang et al., 2006) and the price of recombinant GDNF is high. The properties of E. coli-produced recombinant GDNF may vary from batch to batch, since it is first produced as an inactive protein followed by in vitro renaturation. Finally, GDNF is promiscuous; not only can it activate RET through $GFR\alpha 1$ (weakly also through $GFR\alpha 2$ and $GFR\alpha 3$), but GDNF can also activate completely different receptors: neural cell adhesion molecule NCAM and syndecan glycoproteins that carry GDNF-binding heparan sulphate side chains (Bespalov et al., unpublished) (Sariola and Saarma, 2003). These pleiotropic GDNF actions can lead to multiple side-effects.

Since mammalian cells secrete active GDNF under strict quality control, gene- and cell therapy approach may help to overcome the immunogenic and inflammation response problems associated with E. coli-produced recombinant GDNF. Viral vectors and implantable devices containing polymer-encapsulated genetically modified cells that secrete GDNF (Sautter et al., 1998) could be used in the therapy of Parkinson's disease. Unfortunately, these strategies may increase the risk of cancer, because constant RET activation by unregulated and continuously produced GDNF may lead to malignancy. For instance, GDNF-overexpressing transgenic mice develop testicular cancer (Meng et al., 2001). Unlike gene- or cell therapy, small molecules do not trigger permanent RET activation, since they are delivered at defined time intervals and they are rapidly degraded in the organism. The risk of carcinogenesis is further reduced by the fact that GDNF-mimetics are partial agonists.

SUMMARY OF THE INVENTION

The present invention is related to a method of treating a disorder that can be treated by contacting, activating or inhibiting a $GFR\alpha$/RET receptor complex in a subject in need of treatment thereof, comprising administering to the subject an effective amount of a compound having binding and/or modulation specificity for a $GFR\alpha 1$ receptor molecule, thereby treating the disorder.

All aspects of the invention described in relation to administering a compound or composition or substance to a subject also should be understood to relate to use of the compound or composition or substance for treatment of the subject; or for manufacture of a medicament (useful for) treatment of the condition for which the subject is in need of treatment.

Likewise, all compounds (or salts, esters, or pro-drugs thereof) described herein as useful for these purposes are themselves an aspect of the invention. Similarly, compositions comprising one or more of these compounds and a pharmaceutically acceptable diluent, excipient, or carrier, are an aspect of the invention. Similarly, unit dose formulations of one or more of the compounds are an aspect of the invention. Additionally, a medical device such as a syringe that contains the compound or composition is an aspect of the invention.

The disorders targeted by the present invention include Alzheimer's disease, Huntington's disease, amyotrophic lateral sclerosis, Rett syndrome, epilepsy, Parkinson's disease, spinal cord injury, stroke, hypoxia, ischemia, brain injury, diabetic neuropathy, peripheral neuropathy, nerve transplantation complications, motor neuron disease, multiple sclerosis, HIV dementia, peripheral nerve injury, hearing loss, depression, obesity, metabolic syndrome, pain, cancer, and other conditions involving degeneration or dysfunction of cells expressing GFRα/RET.

Also disclosed are the compounds, or salts or esters thereof, which can inhibit and/or activate the GFRα/RET receptor complex.

In jurisdictions that forbid the patenting of methods that are practiced on the human body, the following restrictions are intended: (1) the selecting of a human subject shall be construed to be restricted to selecting based on testing of a biological sample that has previously been removed from a human body and/or based on information obtained from a medical history, patient interview, or other activity that is not practiced on the human body; and (2) the administering of a composition to a human subject shall be restricted to prescribing a controlled substance that a human subject will self-administer by any technique (e.g., orally, inhalation, topical application, injection, insertion, etc.); or that a person other than the prescribing authority shall administer to the subject. For each jurisdiction, the broadest reasonable interpretation that is consistent with laws or regulations defining patentable subject matter is intended. In jurisdictions that do not forbid the patenting of methods that are practiced on the human body, the selecting of subjects and the administering of compositions includes both methods practiced on the human body and also the foregoing activities.

The "summary of invention" heading is not intended to be restrictive or limiting. The invention also includes all aspects described in the detailed description or figures as originally filed. The original claims appended hereto also define aspects that are contemplated as the invention and are incorporated into this summary by reference.

In addition to the foregoing, the invention includes, as an additional aspect, all embodiments of the invention narrower in scope in any way than the variations specifically mentioned above. For example, although aspects of the invention may have been described by reference to a genus or a range of values for brevity, it should be understood that each member of the genus and each value or sub-range within the range is intended as an aspect of the invention. Likewise, various aspects and features of the invention can be combined, creating additional aspects which are intended to be within the scope of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE FIGURES

FIG. 2: Validation of GFLs-signaling-mimetics using proprietary cell-based luciferase-reporter system. Structures of several compounds screened are as follows: compound 243G7 has a structure of Formula (VIII), described below; compound 299B5 has a structure of formula (X), described below; compound 290A11 has a structure of:

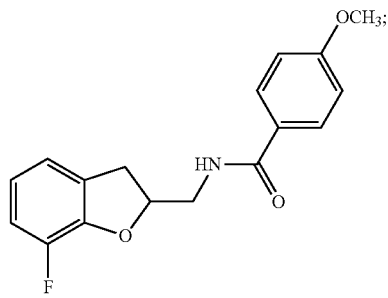 [SMILES: COc1ccc(C(=O)NCC2Cc3cccc(F)c3O2)cc1]

compound 319H6 has a structure of

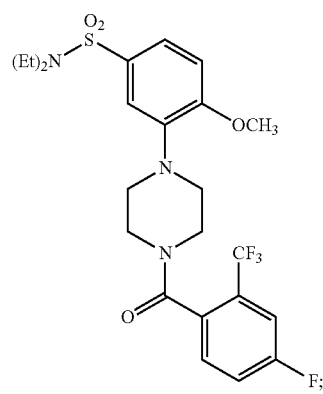

and compound 375F4 has a structure of

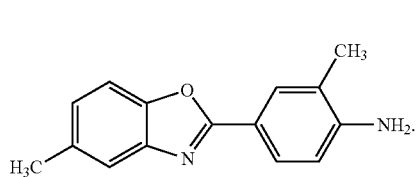 [SMILES: Cc1ccc2oc(-c3ccc(N)c(C)c3)nc2c1]

Figure 3:
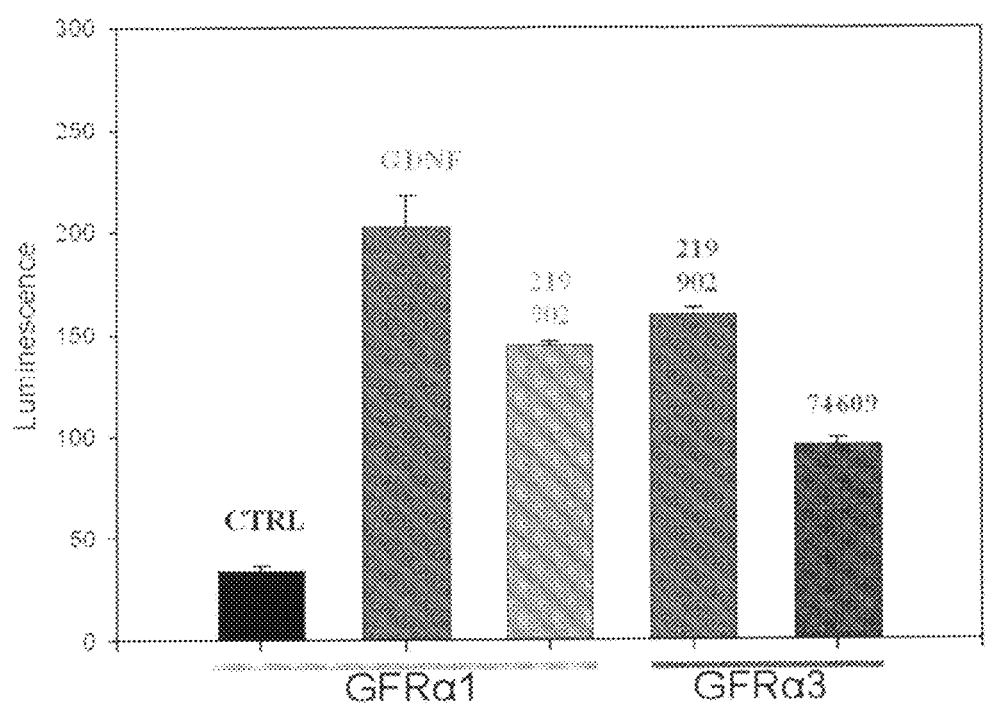

FIG. 3: Detection of GFL-mimetics with RET-ELISA assay. GFL-mimetics activate RET via GFRα1 and GFRα3. Compound 219902 has a structure of

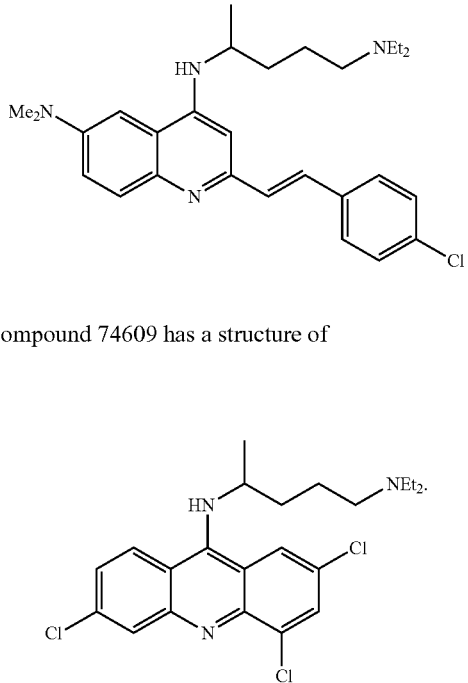

and compound 74609 has a structure of

Figure 4:
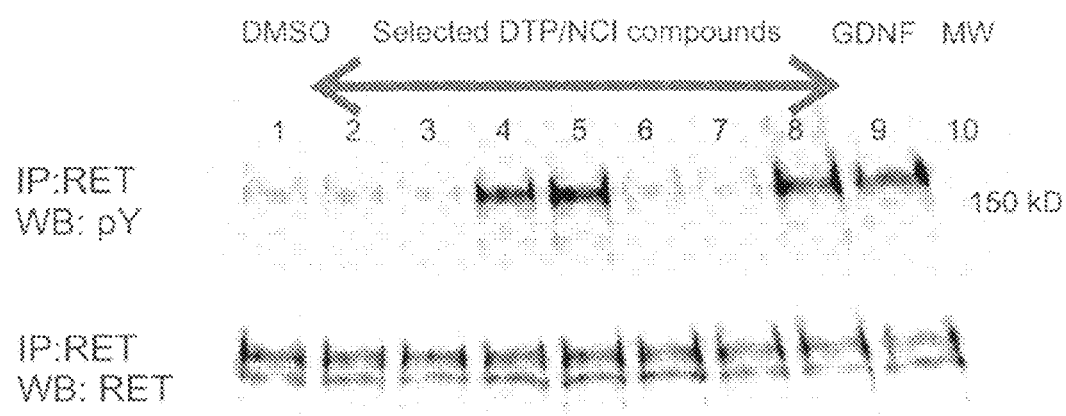

FIG. 4: Selected GFL-mimetics can potently activate RET via GFRα as revealed by phosphorylation assay. WB: Western blotting. IP: immunoprecipitation. pY: aniti-phospho-tyrosine antibodies. The asterisk indicates GLF-mimetic compounds that induce RET activation. The lane numbers and compounds were as follows: 1) dimethyl sulfoxide (DMSO); 2) inactive compound chloroquine having a structure

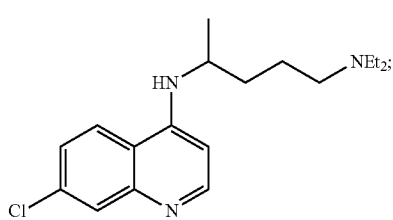

3) inactive compound 13005 having a structure

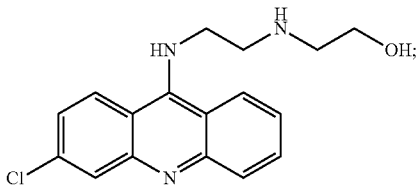 [SMILES: OCCNCCNc1c2ccccc2nc2cc(Cl)ccc12]

4) active compound 219902, having a structure of

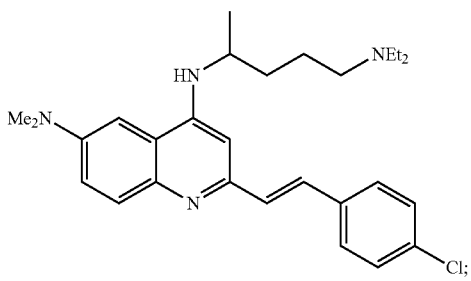

5) active compound 143511 having a structure

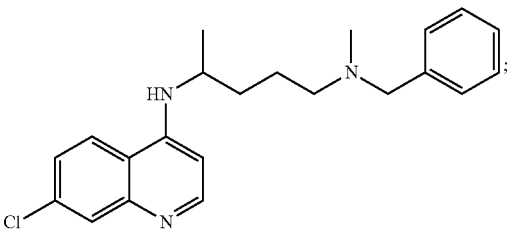 [SMILES: CC(CCCN(C)Cc1ccccc1)Nc1ccnc2cc(Cl)ccc12]

6) inactive compound 349051 having a structure

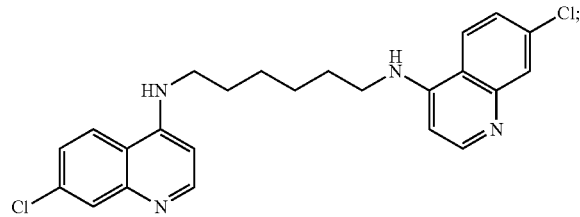 [SMILES: Clc1ccc2c(NCCCCCCNc3ccnc4cc(Cl)ccc34)ccnc2c1]

7) inactive compound 108 having a structure

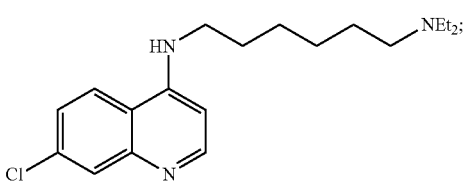

8) active compound 292651 having a structure

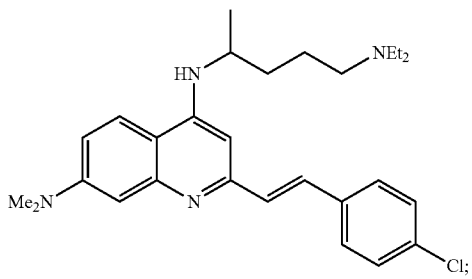

9) GDNF; and 10) molecular weight marker (MW).

Figure 5:
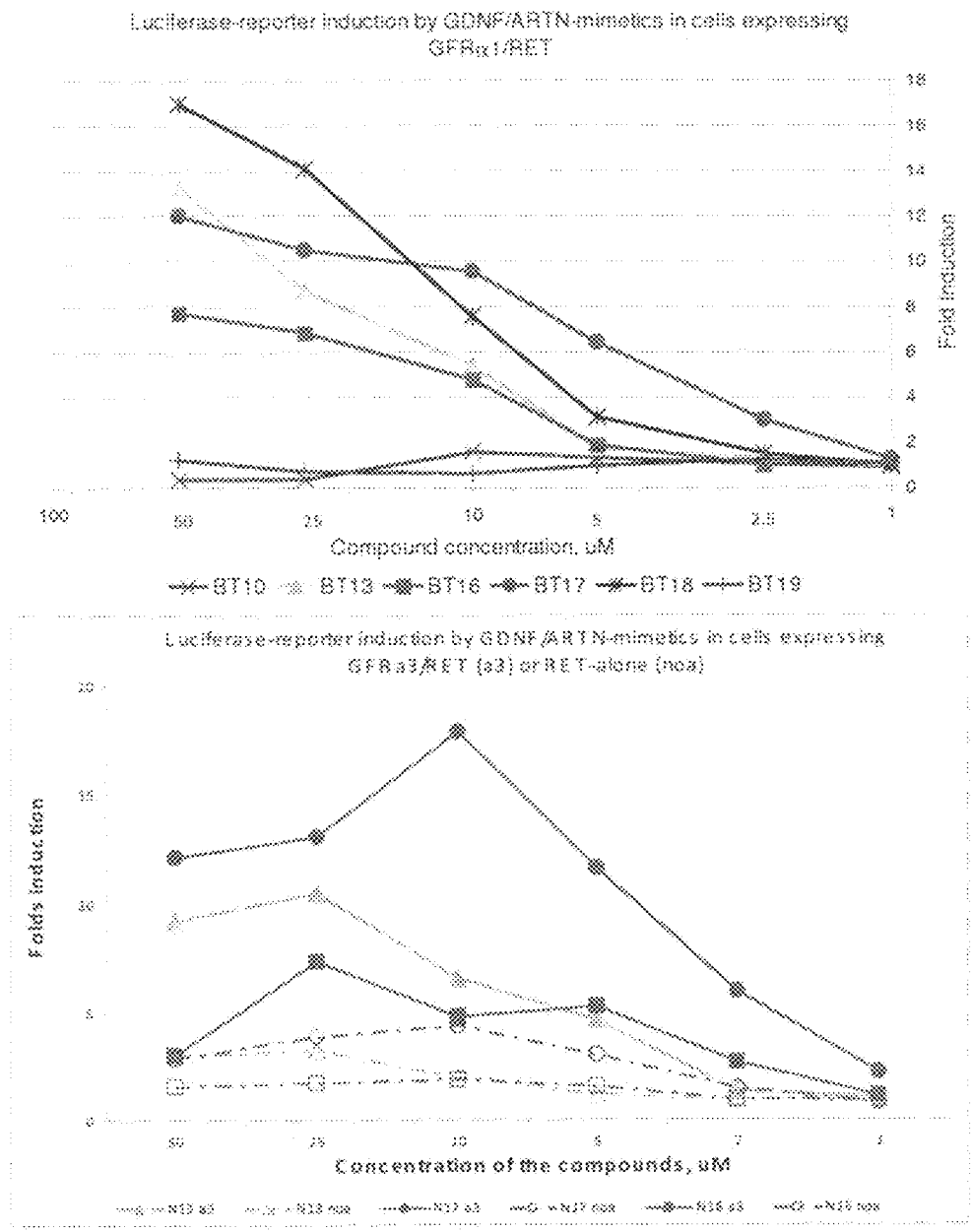

FIG. 5 shows the dose-response for the compounds applied to the GFRα1/RET-expressing cells (upper panel), GFRα3/RET- or RET-expressing reporter cell lines (lower panel). The signaling cascade activated by GFRα/RET leads to the activation of MAPK, which leads to induction of the luciferase reporter. The compounds BT13, BT16, BT17 and can in a dose-dependent manner induce luciferase expression in GFRα1/RET and in GFRα3/RET-expressing reporter cell lines. No significant effect was observed in cells expressing RET alone. Compound BT18 was active in GFRα1/RET-cell line. GFRα3/RET-expressing cell line (a3): solid lines; RET-expressing cell line (Noa): dashed lines. The structure for BT10 is

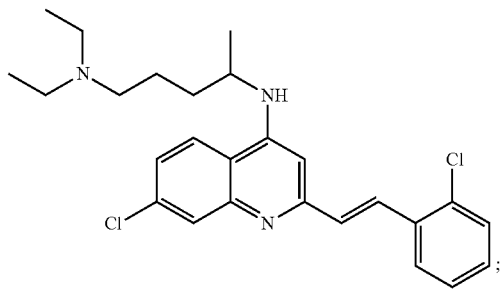 [SMILES: CCN(CC)CCCC(C)Nc1cc(/C=C/c2ccccc2Cl)nc2cc(Cl)ccc12]

the structure for BT13
(alternatively called herein N13) is

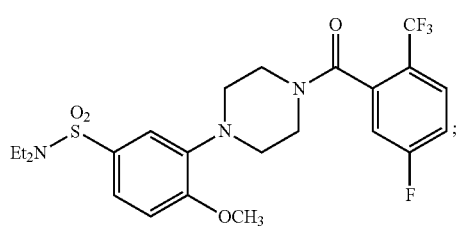

the structure for BT16 (alternatively called herein N16) is

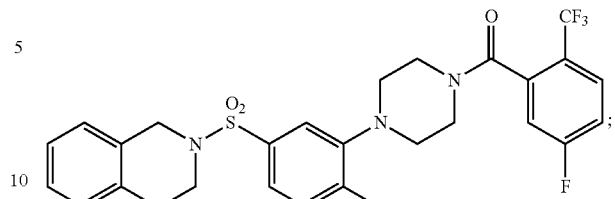

the structure for BT17 (alternatively called herein N17) is

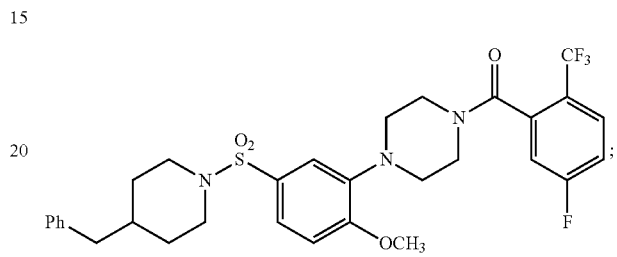

the structure for B18 is

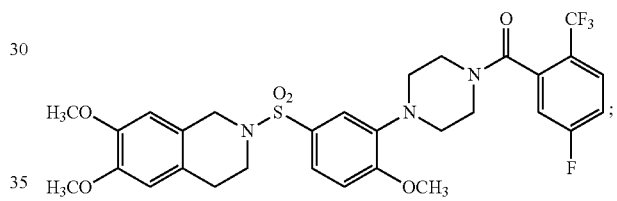

and the structure for B19 is

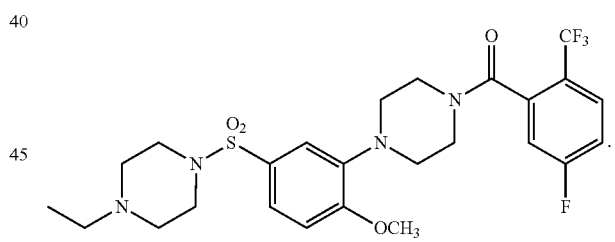

FIG. 6 shows RET phosphorylation induced by novel (BT) GDNF-/ARTN mimetics. The structures for BT10, 13, 16, 17, and 19 are as shown for FIG. 5; and the structure for BT12 is

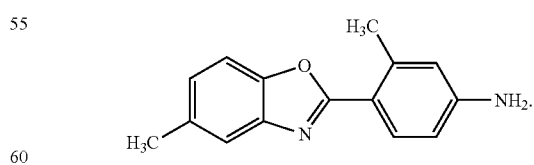

Figure 6A:
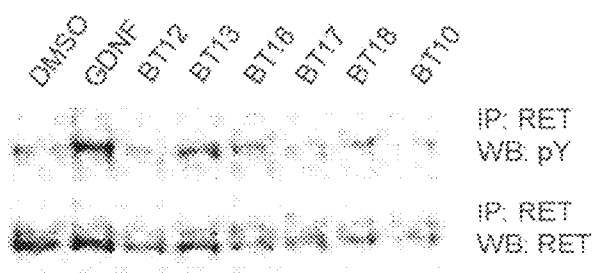

FIG. 6A shows activation of GFRα1/RET by various BT compounds, the structures for which are shown above: MG87 RET fibroblasts were transfected with GFRα1 construct and treated with a BT test compound at 100 μM concentration. The upper panel represents the membrane containing the immunoprecipitated with RET antibodies (IP: RET) lysed that were probed with anti-phosphotyosine antibodies (WB: pY). Compounds BT13 and BT16 strongly activated RET via GFRα1. Compounds BT17 and BT18 are likely the weaker GFRα1/RET agonists. The lower panel shows the same membrane probed with anti-RET antibodies (WB: RET). Dimethyl sulfoxide (DMSO) was used as a negative control. GDNF (100 ng/ml) was used a positive control.

Figure 6B:
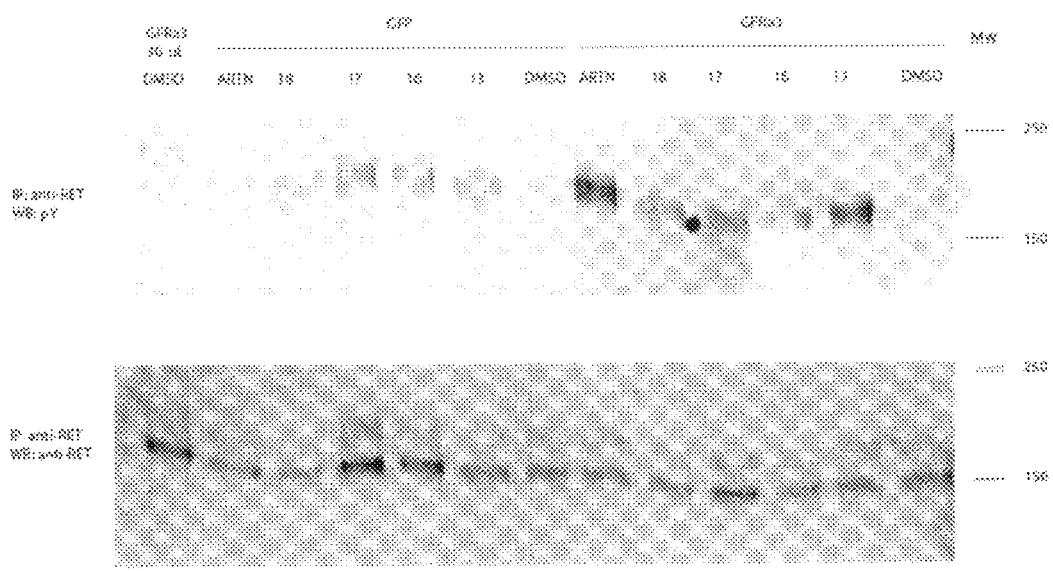

FIG. 6B shows Activation of GFRα3/RET by BT compounds. MG87 RET fibroblasts were transfected with either GFRα3 or GFP constructs and treated with BT compounds, the structures of which are shown above, at 100 µM concentration. The upper panel represents the membrane containing the immunoprecipitated with RET antibodies (IP: anti-RET) lysed that were probed with anti-phosphotyrosine antibodies (WB: pY). Compound BT13 strongly activated RET via GFRα3. Compounds BT16, BT17 and BT18 are likely the weaker GFRα3/RET agonists. The lower panel shows the same membrane probed with anti-RET antibodies (WB: anti-RET). Thirty microliters (30 µl) of DMSO were used as a negative control in GFRα3-transfected cells. ARTN (100 ng/ml) was used a positive control n GFRα3-transfected cells.

Figure 7:
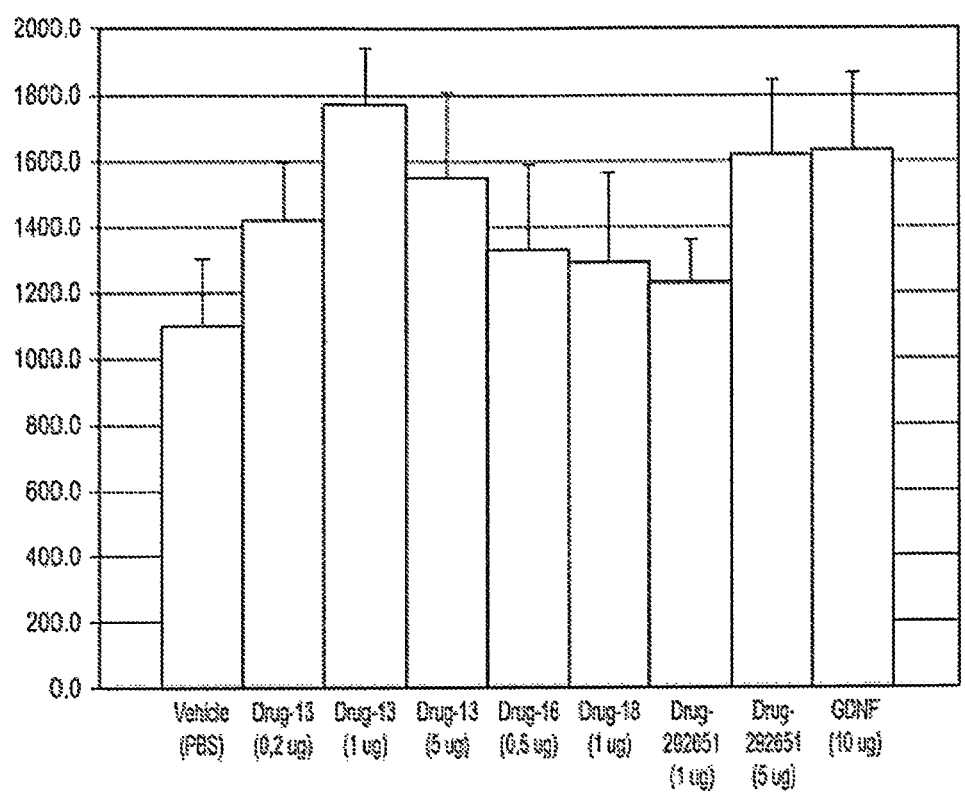

FIG. 7 shows effect of intrastriatal injection of vehicle, GDNF (10 µg) or GDNF mimetics at indicated concentrations (0.2-5 µg) on amphetamine-induced rotation. Rats received vehicle, GDNF or BT GDNF mimetics compounds, the structures of which are shown above, in the striatum three weeks after the lesion was induced by intrastriatal 6-OHDA (28 micrograms). Amphetamine-induced behavior was measured 6 weeks post lesion.

Figure 8:
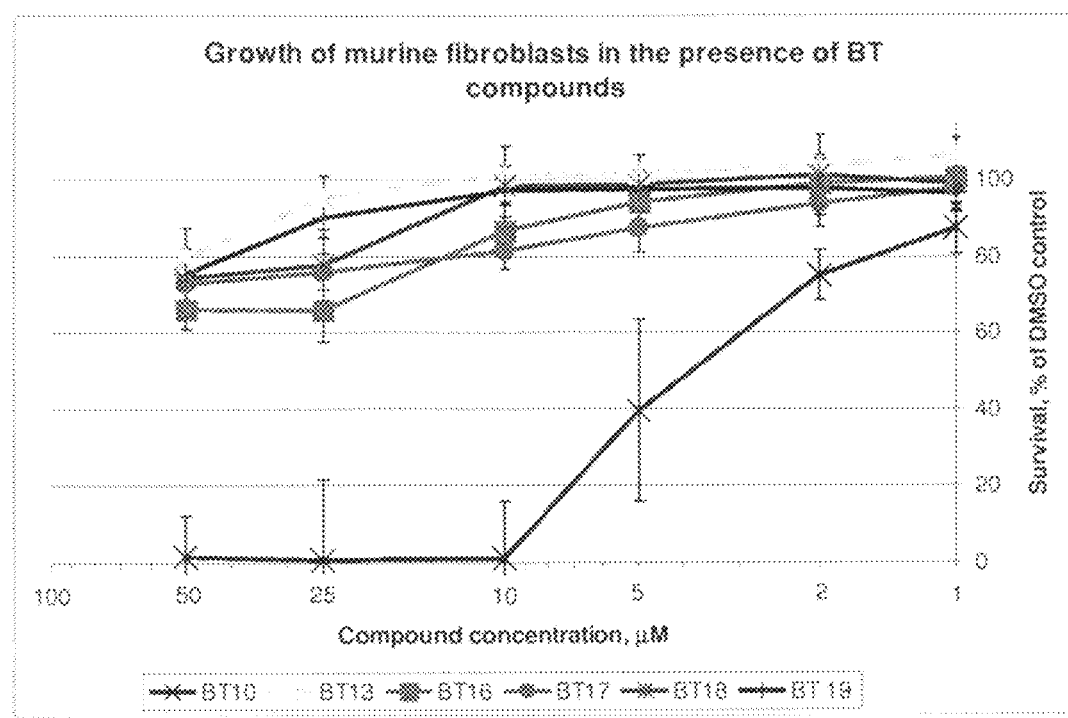

FIG. 8 shows the cell growth of murine fibroblasts in the presence of the indicated BT compounds. The structures of BT10, 13, 16, 17, 18, and 19 are as shown above. The results are represented as percentage of living cells from DMSO control (which is assumed as viability of 100±5 percent). All compounds showed moderate cell growth inhibition at 50 µM concentration (except for BT10 that has showed significant toxicity at concentrations above 2 µM).

Figure 9:
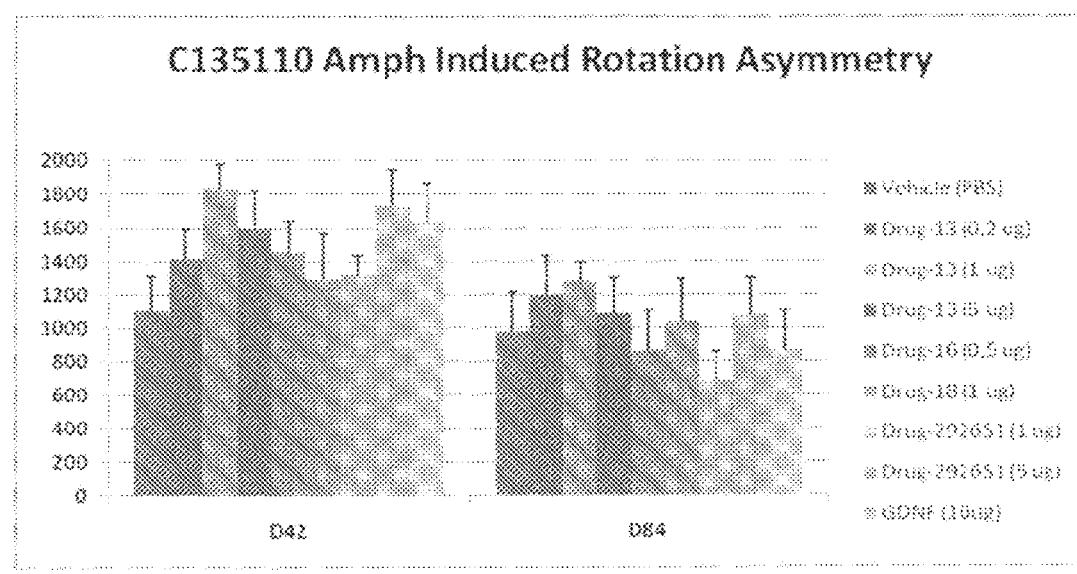

FIG. 9 shows the effect of intrastriatal injection of vehicle or GDNF (10 µg) or a GDNF mimetic (dose indicated) on amphetamine-induced rotation. Structures of the compounds are as indicated above.

DETAILED DESCRIPTION

Disclosed herein are compounds and methods of treating a disorder in a subject, including both neurological and non-neurological disorders, comprising administering to the subject an effective amount of a compound having binding and/or modulation specificity for a GFRα receptor molecules ("GDNF mimetic compounds") or downstream RET signaling ("RET signaling activating compounds"). In some variations of the invention, the compound is administered in a composition that also includes one or more pharmaceutically acceptable diluents, adjuvants, or carriers.

For purposes of the disclosure, treating is considered a success if any of the following therapeutic goals are achieved: symptoms of the disease are ameliorated, alleviated, or diminished; progression of the disease or disease symptoms is slowed or arrested; deterioration or injury is alleviated, partially healed, or fully healed; and/or if the subject makes a partial or complete recovery; and/or other standard-of-care therapies that are more expensive, more difficult to administer, or have less acceptable side-effects can be reduced or eliminated while achieving a similar quality of life.

The disorder can be, for example, Alzheimer's disease, Huntington's disease, amyotrophic lateral sclerosis, Rett syndrome, epilepsy, Parkinson's disease, spinal cord injury, stroke, hypoxia, ischemia, brain injury, diabetic neuropathy, peripheral neuropathy, nerve transplantation complications, motor neuron disease, multiple sclerosis, HIV dementia, peripheral nerve injury, hearing loss, depression, obesity, metabolic syndrome, pain, cancer, or conditions involving degeneration or dysfunction of cells expressing GFRα and/or RET.

The subject can be an animal or a human subject. The animal can be a mammal.

Also disclosed herein are methods of facilitating neural cell survival or promoting neural function, comprising treating a neural cell with a compound having the ability to specifically bind and/or modulate the activity of a GFRα1 receptor molecule. Additionally disclosed herein are compounds that induce downstream RET signaling.

The compound can be a small molecule. In some embodiments, GDNF mimetic compound has a structure of Formula (I),

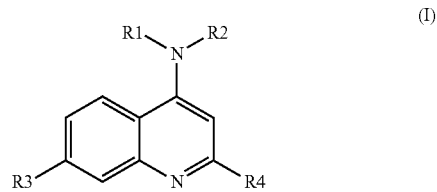

wherein R1 and R2 are independently selected from the group consisting of H, alkyl, aryl, alkylenearyl, acyl, alkoxycarbonyl, aryloxycarbonyl, alkylenearyloxycarbonyl, carbamoyl, alkylcarbamoyl, dialkylcarbamoyl, and alkyleneamino; R3 is independently selected from H, fluorine, chlorine, bromine, iodide, alkyl, aryl, alkylenearyl, acyl, alkoxycarbonyl, aryloxycarbonyl, alkylenearyloxycarbonyl, carbamoyl, alkylcarbamoyl, and dialkyl-carbamoyl and R4 is selected from the group consisting of H, alkyl, aryl, alkylenearyl, alkenylenearyl, hydroxyl; or a pharmaceutically acceptable salt thereof. In some embodiments, R1 and R2 are independently selected from the group consisting of alkyleneamino and hydrogen, where the amino group of the alkyleneamino moiety can be further substituted with one or two alkyl or alkylenearyl (e.g., a benzyl) groups. In various embodiments, R3 is chloro or aminoalkyl. In a specific embodiment, R1 is hydrogen and R2 is alkyleneamino.

In some embodiments, the GDNF mimetic compound has a structure of Formula (II)

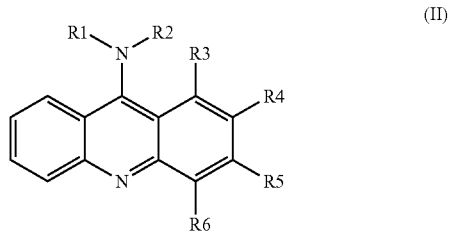

wherein R1 and R2 are independently selected from the group consisting of H, alkyl, aryl, alkylenearyl, acyl, alkoxycarbonyl, aryloxycarbonyl, alkylenearyloxycarbonyl, carbamoyl, alkylcarbamoyl, dialkylcarbamoyl, and alkyleneamino; R3, R4, R5, and R6 are independently selected from H, fluorine, chlorine, bromine, iodide, alkyl, aryl, alkylenearyl, acyl, alkoxycarbonyl, aryloxycarbonyl, alkylenearyloxycarbonyl, carbamoyl, alkylcarbamoyl, and dialkylcarbamoyl; or a pharmaceutically acceptable salt thereof.

In some embodiments, the GDNF mimetic compound has a structure of Formula (III)

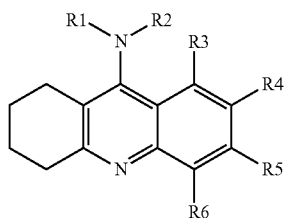

(III)

wherein R1 and R2 are independently selected from the group consisting of H, alkyl, aryl, alkylenearyl, acyl, alkoxycarbonyl, aryloxycarbonyl, alkylenearyloxycarbonyl, carbamoyl, alkylcarbamoyl, dialkylcarbamoyl, and alkyleneamino; R3, R4, R5, and R6 are independently selected from H, fluorine, chlorine, bromine, iodide, alkyl, aryl, alkylenearyl, acyl, alkoxycarbonyl, aryloxycarbonyl, alkylenearyloxycarbonyl, carbamoyl, alkylcarbamoyl, and dialkylcarbamoyl; or a pharmaceutically acceptable salt thereof.

In some embodiments, the GDNF mimetic compound has a structure of Formula (IV)

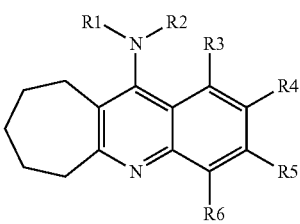

(IV)

wherein R1 and R2 are independently selected from the group consisting of H, alkyl, aryl, alkylenearyl, acyl, alkoxycarbonyl, aryloxycarbonyl, alkylenearyloxycarbonyl, carbamoyl, alkylcarbamoyl, dialkylcarbamoyl, alkyleneamino; R3, R4, R5, and R6 are independently selected from H, fluorine, chlorine, bromine, iodide, alkyl, aryl, alkylenearyl, acyl, alkoxycarbonyl, aryloxycarbonyl, alkylenearyloxycarbonyl, carbamoyl, alkylcarbamoyl, and dialkylcarbamoyl; or a pharmaceutically acceptable salt thereof.

In some embodiments, the RET signaling activating compound has a structure of Formula (V)

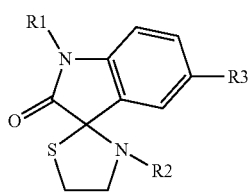

(V)

wherein R1 and R2 are independently selected from the group consisting of H, alkyl, aryl, alkylenearyl, acyl, alkoxycarbonyl, aryloxycarbonyl, alkylenearyloxycarbonyl, carbamoyl, alkylcarbamoyl, dialkylcarbamoyl, alkyleneamino; R3 is independently selected from H, fluorine, chlorine, bromine, iodide, alkyl, aryl, alkylenearyl, acyl, alkoxy, alkoxycarbonyl, aryloxycarbonyl, alkylenearyloxycarbonyl, carbamoyl, alkylcarbamoyl, and dialkylcarbamoyl; or a pharmaceutically acceptable salt thereof.

In some embodiments, the RET signaling activating compound has a structure of Formula (VI)

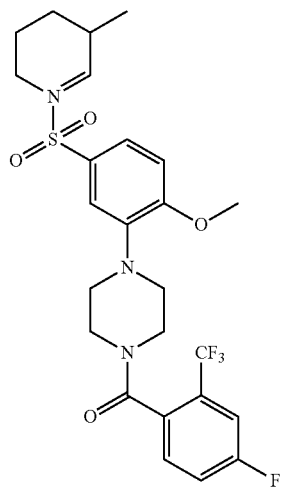

(VI)

or a pharmaceutically acceptable salt thereof.

In some embodiments, RET signaling activating compound has a structure of Formula (VII)

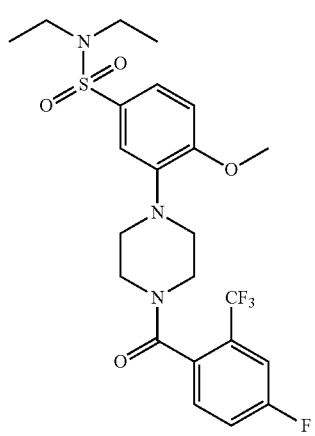

(VII)

or a pharmaceutically acceptable salt thereof.

In some embodiments, the RET signaling activating compound has a structure of Formula (VIII)

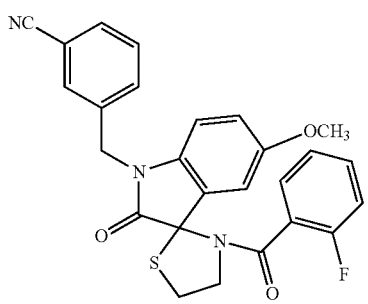

(VIII)

or a pharmaceutically acceptable salt thereof.

In some embodiments, the RET signaling activating compound has a structure of Formula (IX)

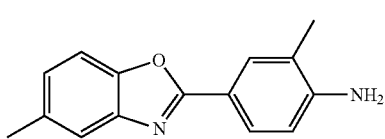

(IX)

or a pharmaceutically acceptable salt thereof.

In some embodiments, the RET signaling activating compound has a structure of Formula (X)

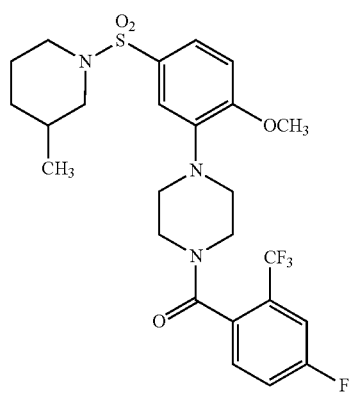

(X)

or a pharmaceutically acceptable salt thereof.

In some embodiments, the RET signaling activating compound has a structure of Formula (XI)

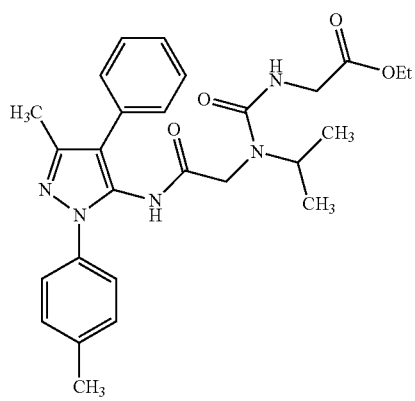

(XI)

or a pharmaceutically acceptable salt thereof.

In some embodiments, the RET signaling activating compound has a structure of Formula (XII)

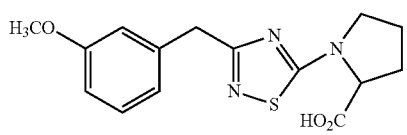

(XII)

or a pharmaceutically acceptable salt thereof.

In some embodiments, the RET signaling activating compound has a structure of Formula (XIII)

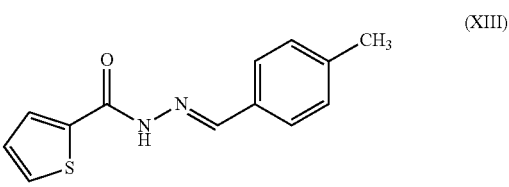 [SMILES: Cc1ccc(/C=N/NC(=O)c2cccs2)cc1]

(XIII)

or a pharmaceutically acceptable salt thereof.

In some embodiments, the RET signaling activating compound has a structure of any one of the following formulae

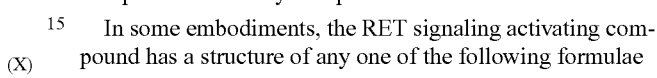

(XIV)

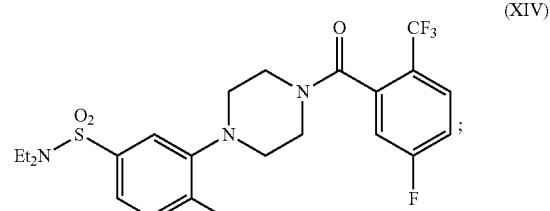

(XV)

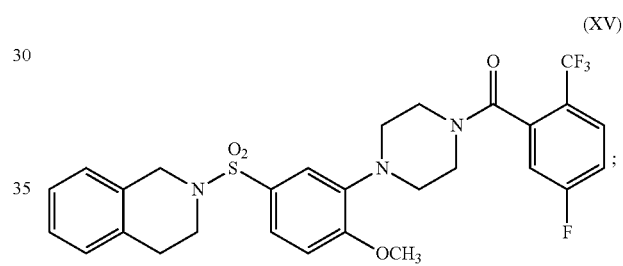

(XVI)

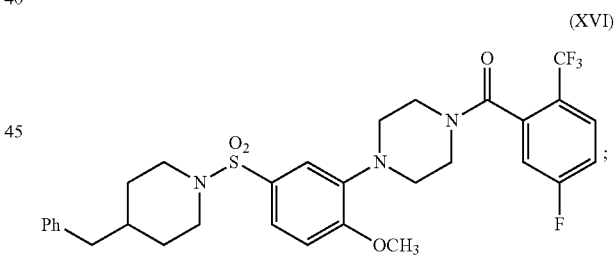

(XVII)

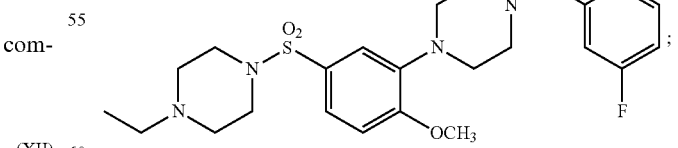

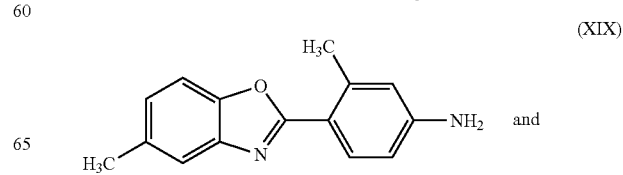

(XIX)

-continued (XVIII)

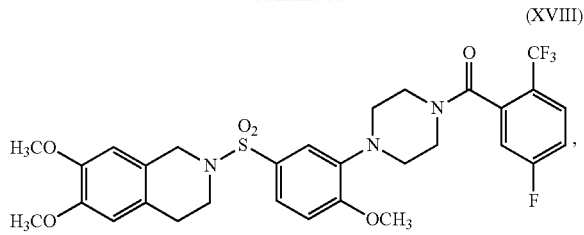

or a pharmaceutically acceptable salt thereof.

In various cases, the RET signaling activating compound has a structure of Formula (XX):

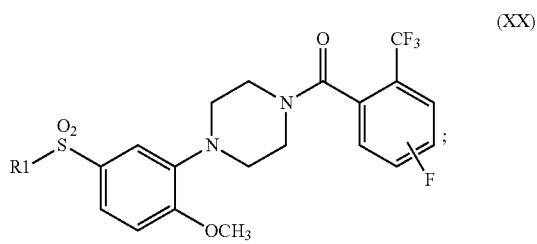

(XX)

wherein R1 is a cyclic or acyclic amino group, or a pharmaceutically acceptable salt thereof. Non-limiting examples of R1 groups include dialkyl amino, piperidinyl, substituted piperidinyl, piperazinyl; substituted piperazinyl; tetrahydroisoquinolinyl; and substituted tetrahydroisoquinolinyl.

As used herein, the term "alkyl" refers to straight chained and branched hydrocarbon groups containing carbon atoms, typically methyl, ethyl, and straight chain and branched propyl and butyl groups. Unless otherwise indicated, the hydrocarbon group can contain up to 20 carbon atoms. The term "alkyl" includes "bridged alkyl," i.e., a $C_6$-$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halo, amino, and sulfonyl. An "alkoxy" group is an alkyl group having an oxygen substituent, e.g., —O-alkyl.

The term "alkenyl" refers to straight chained and branched hydrocarbon groups containing carbon atoms having at least one carbon-carbon double bond. Unless otherwise indicated, the hydrocarbon group can contain up to 20 carbon atoms. Alkenyl groups can optionally be substituted, for example, with hydroxy (OH), halo, amino, and sulfonyl.

As used herein, the term "alkylene" refers to an alkyl group having a further defined substituent. For example, the term "alkylenearyl" refers to an alkyl group substituted with an aryl group, and "alkyleneamino" refers to an alkyl groups substituted with an amino group. The amino group of the alkyleneamino can be further substituted with, e.g., an alkyl group, an alkylenearyl group, an aryl group, or combinations thereof. The term "alkenylene" refers to an alkenyl group having a further defined substituent.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like. An "aryloxy" group is an aryl group having an oxygen substituent, e.g., —O-aryl.

As used herein, the term "acyl" refers to a carbonyl group, e.g., C(O). The acyl group is further substituted with, for example, hydrogen, an alkyl, an alkenyl, an aryl, an alkenylaryl, an alkoxy, or an amino group. Specific examples of acyl groups include, but are not limited to, alkoxycarbonyl (e.g., C(O)—Oalkyl); aryloxycarbonyl (e.g., C(O)—Oaryl); alkylenearyloxycarbonyl (e.g., C(O)—Oalkylenearyl); carbamoyl (e.g., C(O)—$NH_2$); alkylcarbamoyl (e.g., C(O)—NH (alkyl)) or dialkylcarbamoyl (e.g., C(O)—NH(alkyl)$_2$).

As used herein, the term "amino" refers to a nitrogen containing substituent, which can have zero, one, or two alkyl, alkenyl, aryl, alkylenearyl, or acyl substituents. An amino group having zero substituents is —$NH_2$.

As used herein, the term "halo" or "halogen" refers to fluoride, bromide, iodide, or chloride.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Formulations

The compounds disclosed herein can also be admixed, encapsulated, conjugated or otherwise associated with other molecules, molecule structures or mixtures of compounds, as for example, liposomes, carriers, diluents, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Further disclosed herein are pharmaceutical compositions and formulations which include the compounds described. The pharmaceutical compositions can be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical formulations, which may conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions can be formulated into any of many possible dosage forms such as, but not limited to, tablets, capsules, gel capsules, liquid syrups, soft gels, suppositories, and enemas. The compositions can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension may also contain stabilizers.

Pharmaceutical compositions include, but are not limited to, solutions, emulsions, foams and liposome-containing formulations. The pharmaceutical compositions and formulations of the present invention may comprise one or more penetration enhancers, carriers, excipients, diluents, or other active or inactive ingredients.

Emulsions are typically heterogeneous systems of one liquid dispersed in another in the form of droplets usually exceeding 0.1 µm in diameter. Emulsions can contain additional components in addition to the dispersed phases, and the active drug which is present as a solution in either the aqueous phase, oily phase, or itself as a separate phase. Microemulsions are included as an embodiment of the disclosure. Emulsions and their uses are well known in the art and are further described in U.S. Pat. No. 6,287,860, which is incorporated herein in its entirety.

Formulations can include liposomal formulations. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions disclosed herein can also include surfactants. The use of surfactants in drug products, formulations and in emulsions is well known in the art. Surfactants and their uses are further described in U.S. Pat. No. 6,287,860, which is incorporated herein in its entirety.

In one embodiment, disclosed herein are formulations comprising one or more penetration enhancers to effect the efficient delivery of the compounds disclosed herein. In addition to aiding the diffusion of non-lipophilic drugs across cell membranes, penetration enhancers also enhance the permeability of lipophilic drugs. Penetration enhancers can be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the compounds of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compounds are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Compounds of the invention may be delivered orally, in granular form including sprayed dried particles, or complexed to form micro or nanoparticles. Complexing agents and their uses are further described in U.S. Pat. No. 6,287,860, which is incorporated herein in its entirety. Oral formulations and their preparation are described in detail in U.S. application Ser. Nos. 09/108,673, 09/315,298, and 10/071,822, each of which is incorporated herein by reference in their entirety.

Compositions and formulations for parenteral, intrathecal or intraventricular administration can include sterile aqueous solutions which can also contain buffers, diluents and other suitable additives such as, but not limited to, penetration enhancers, carrier compounds and other pharmaceutically acceptable carriers or excipients.

When necessary, in order to promote penetration of the blood-brain-barrier (BBB), the active compounds can be administered by using various now strategies for gaining drug access to the brain. Various strategies known in the art for increasing transport across the BBB can be adapted to the compounds of the invention to thereby enhance transport of the modulators across the BBB (for reviews of such strategies, see e.g., Pardridge. *Trends in Biotechnol.* 12:239-245 (1994); Van Bree, et al. *Pharm. World Sci.* 15:2-9 (1993); and Pardridge, et al. *Pharmacol. Toxicol.* 71:3-10 (1992)). In one approach, the compound is chemically modified to form a prodrug with enhanced transmembrane transport. Suitable chemical modifications include covalent linking of a fatty acid to the compound through an amide or ester linkage (see e.g., U.S. Pat. No. 4,933,324 and PCT Publication WO 89/07938; U.S. Pat. No. 5,284,876; Toth, et al. *J. Drug Target.* 2:217-239 (1994); and Shashoua, et al. *J. Med. Chem.* 27:659-664 (1984)) and glycating the compound (see e.g., U.S. Pat. No. 5,260,308). Also, N-acylamino acid derivatives may be used in a modulator to form a "lipidic" prodrug (see e.g., U.S. Pat. No. 5,112,863).

In another approach for enhancing transport across the BBB, a peptidic or peptidomimetic compound is conjugated to a second peptide or protein, thereby forming a chimeric protein, wherein the second peptide or protein undergoes absorptive-mediated or receptor-mediated transcytosis through the BBB. Accordingly, by coupling a compound as disclosed herein to this second peptide or protein, the chimeric protein is transported across the BBB. The second peptide or protein can be a ligand for a brain capillary endothelial cell receptor ligand. For example, a preferred ligand is a monoclonal antibody that specifically binds to the transferrin receptor on brain capillary endothelial cells (see e.g., U.S. Pat. Nos. 5,182,107 and 5,154,924 and PCT Publications WO 93/10819 and WO 95/02421). Other suitable peptides or proteins that can mediate transport across the BBB include histones (see e.g., U.S. Pat. No. 4,902,505) and ligands such as biotin, folate, niacin, pantothenic acid, riboflavin, thiamin, pryridoxal and ascorbic acid (see e.g., U.S. Pat. Nos. 5,416, 016 and 5,108,921). Additionally, the glucose transporter GLUT-1 has been reported to transport glycopeptides (L-serinyl-β-D-glucoside analogues of [Met5]enkephalin) across the BBB (Polt et al. *Proc. Natl. Acad. Sci. USA* 91:7114-1778 (1994)). Accordingly, a compound can be coupled to such a glycopeptide to target the modulator to the GLUT-1 glucose transporter. For example, a compound which is modified at a free amine with the modifying group Aic (3-(O-aminoethyl-iso)-cholyl, a derivative of cholic acid having a free amino group) can be coupled to a glycopeptide through the amino group of Aic by standard methods. Chimeric proteins can be formed by recombinant DNA methods (e.g., by formation of a chimeric gene encoding a fusion protein) or by chemical crosslinking of the modulator to the second peptide or protein to form a chimeric protein. Numerous chemical crosslinking agents are known in the art (e.g., commercially available from Pierce, Rockford Ill.). A crosslinking agent can be chosen which allows for high yield coupling of the modulator to the second peptide or protein and for subsequent cleavage of the linker to release bioactive modulator. For example, a biotin-avidin-based linker system may be used.

In yet another approach for enhancing transport across the BBB, the compound is encapsulated in a carrier vector which mediates transport across the BBB. For example, the compound can be encapsulated in a liposome, such as a positively charged unilamellar liposome (see e.g., PCT Publications WO 88/07851 and WO 88/07852) or in polymeric microspheres (see e.g., U.S. Pat. No. 5,413,797; U.S. Pat. No. 5,271,961; and U.S. Pat. No. 5,019,400). Moreover, the carrier vector can be modified to target it for transport across the BBB. For example, the carrier vector (e.g., liposome) can be covalently modified with a molecule which is actively transported across the BBB or with a ligand for brain endothelial cell receptors, such as a monoclonal antibody that specifically binds to transferrin receptors (see e.g., PCT Publications WO 91/04014 and WO 94/02178).

In still another approach to enhancing transport of the modulator across the BBB, the compound can be coadministered with another agent which functions to permeabilize the BBB. Examples of such BBB "permeabilizers" include bradykinin and bradykinin agonists (see e.g., U.S. Pat. No. 5,112,596) and peptidic compounds disclosed in U.S. Pat. No. 5,268,164.

Dosing

The selection of formulations and administration (dosing) is determined, e.g., by dose-response, toxicity, and pharmacokinetic studies. Dosing is dependent on severity and responsiveness of the disease state to be treated, with the course of treatment lasting from several days to several months, or until a cure is effected, or a diminution of the disease state or disease symptoms is achieved. Dosing may continue indefinitely for chronic disease states or conditions for which diminution but no cure can be achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

Assaying

Also disclosed are methods of assaying a compound for binding and/or modulating a GFRα receptor molecule or downstream RET signaling, e.g., a GDNF mimetic. The assay can provide high throughput analyses of compounds. For example, cells expressing GFRα1 are contacted with a compound of interest and an increase in cell growth indicates whether the compound is a GDNF mimetic, where cell growth of the mimetic assay is compared to a background control experiment with no compound. In some cases, the cells are cells that express luciferase as well as GFRα1, and the indicator of cell growth is luciferase. Measurement of cell growth can be by measuring luminescence of the cell-compound mixture.

Also contemplated are assays in which the cells naturally or recombinantly express other receptors of interest, e.g., GFRα2, GFRα3, GFRα4. In some variations of the invention, compounds are selected that are specific for a single receptor selected from the group consisting of GFRα1, GFRα2, GFRα3, and GFRα4. In other cases, compounds are selected that modulate two, three, or all four of these receptors.

Figure 1:
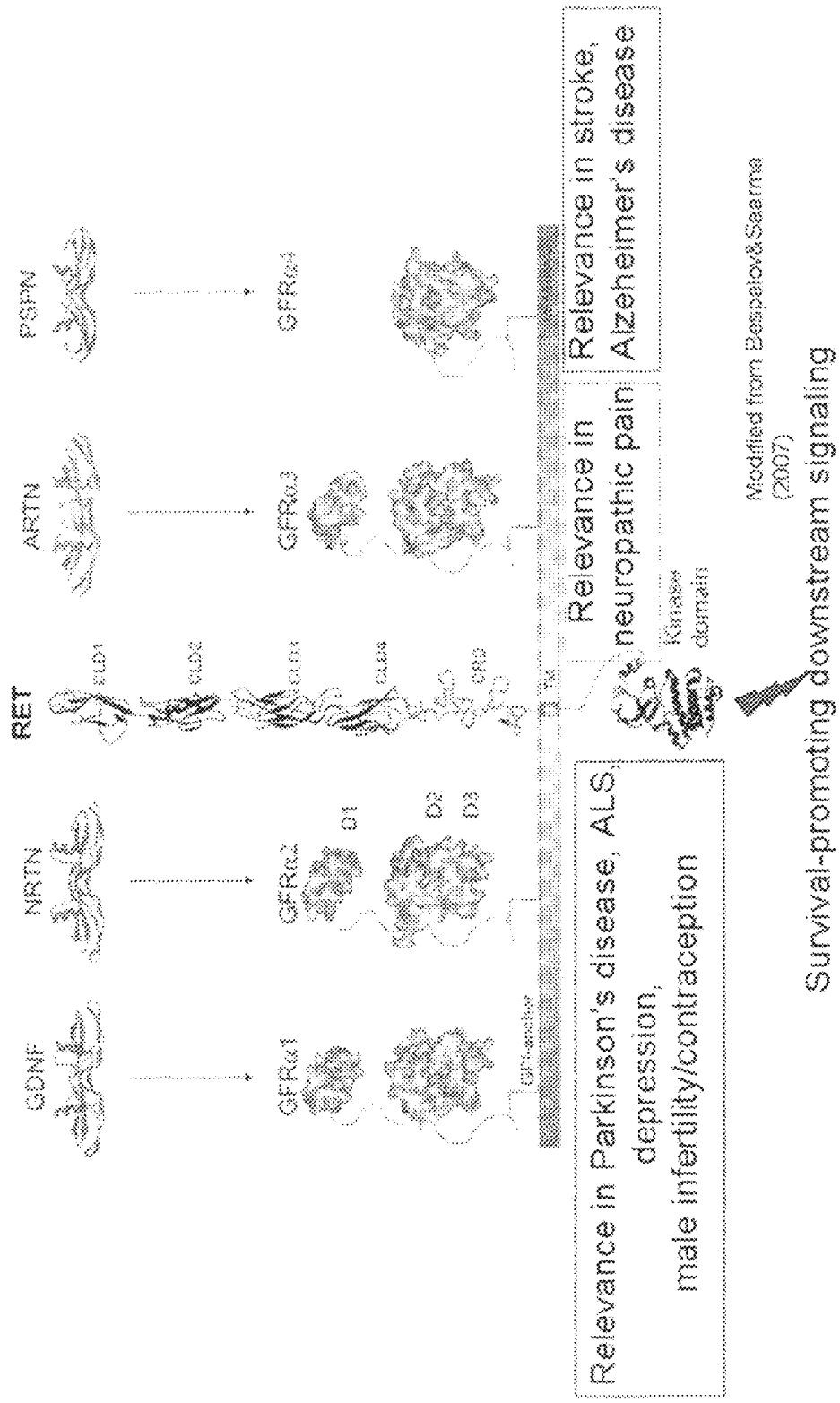
FIG. 1: GDNF family ligands (GFLs) and their receptors. GFLs can not bind the signal-transducing receptor RET directly but require glycosylphosphatidylinositol (GPI)-anchored GFRα. GDNF, neurturin (NRTN), artemin (ARTN) and persephin (PSPN) can all interact with and signal through GFRα/RET receptor complexes. TM—transmembrane domain. All proteins are represented as solid ribbons.

The assays of the invention also can be practiced using a positive control, e.g., a natural ligand for the receptor(s) of interest. In this way, receptor binding compounds can be selected that inhibit ligand-mediated activation of GFRα1, GFRα2, GFRα3, and/or GFRα4. Preferred ligand receptor combinations are depicted in FIG. 1. This figure also depicts exemplary disease indications for compounds that mimic or modulate or interfere with specific ligand/receptor interactions.

Another method disclosed herein comprises a double antibody sandwich ELISA assay to evaluate a compound as a GDNF mimetic, which in some embodiments, can provide quantitative measurement of the mimetic's activity. Cells expressing RET and GFRα1 (or one of the other receptors of interest) are contacted with a compound of interest, then contacted first with an anti-RET antibody then with an anti-pY antibody, such as a mouse anti-pY antibody, to form a double antibody sandwich, where formation of the double antibody sandwich indicates the compound as a GDNF mimetic. In some cases, detection of the sandwich can be by indirect detection, such as, when the anti-pY antibody is a mouse antibody, contacting the sandwich with a secondary anti-mouse HRP-conjugated antibody and a chemiluminescent reagent, such as ECL reagent, and measuring the resulting luminescence.

EXAMPLES

The following Examples have been included to provide illustrations of the presently disclosed subject matter. In light of the present disclosure and the general level of skill in the art, those of skill will appreciate that the following Examples are intended to be exemplary only and that numerous changes, modifications and alterations can be employed without departing from the spirit and scope of the presently disclosed subject matter.

Methods
Cell Lines.
MG87RET murine fibroblasts stably transfected with RET proto-oncogene (Leppänen et al., 2004). N18 rat/mouse glioma/neuroblastoma cells were from ATCC.

Animals.
Superior cervical ganglia were isolated from P0-P2 Wistar rats. The use of experimental animals was approved by the Committee for Animal Experiments of the University of Helsinki, and the chief veterinarian of the County Administrative Board permission (HY 55-06).

Proteins.
GDNF, ARTN, were obtained from PeproTech Ltd. NGF was purchased from Promega. Concentration of all GFLs was checked by microBCA kit (Pierce) using BSA as a standard.

Plasmids.
Full-length flag-tagged rat Gfrα1 cDNA (Leppänen et al., 2004) subcloned into in pcDNA3 (Invitrogen). Full-length human GFRα1 cDNA (Sidorova et al., unpublished) subcloned in pcDNA6 (Invitrogen). Full-length human GFRα3 cDNA (Wang et al., 2006). Full-length human RET (long isoform) (Runeberg-Roos et al., 2007) in pCR3.1 (Invitrogen). The MAPK activation detection system (Baloh et al., 2000) and PathDetect Elk-1 (Stratagene) both of which include two plasmids. First one constitutively expresses MAPK pathway specific fusion transactivator, that consists of activation domain of Elk-1 and DNA-binding domain of the yeast GAL4 protein (Gal4-Elk1). The other plasmid, Gal4-Luc, carries luciferase gene under the control of a synthetic promoter containing the yeast GAL4 binding sequences.

Generation of stable cell lines. MG87RET murine fibroblast were plated on 35 mM dishes and transfected with 4 μg of G4-Luc, Gal4-Elk (Baloh et al., 2000) and GFRα1 expressing plasmid ("αLUC" cells) or empty vector ("NOα" cells) containing neomycin-resistance gene in ratio 4:1:1 using Lipofectamine 2000 (Invitrogen) for DNA delivery as described by manufacturer. The following day, cells were trypsinized and plated in low density on 10-cm tissue culture dishes. Stable transformants were selected in the presence of 500-750 μg/ml geneticin (Invitrogen). Established cell lines were maintained in DMEM, 10% fetal bovine serum (FBS), 100 μg/ml Normocin (Invivogene), 2 μg/ml of puromycin, 500 μg/ml of geneticin, 15 mM HEPES, pH 7.2. Pathdetect Elk-1 system and human GFRα1-expressing plasmid ("Strat-Luc" cells) or empty vector (control cell line "NOStratis") cells were selected and maintained in the DMEM, 10% FBS, 100 μg/ml Normocin (Invivogene), 2 μg/ml of puromycin, 500 μg/ml of G418, 2 μg/ml of blasticidin S, 15 mM HEPES, pH 7.2.

Detection of GDNF Mimetics Using Reporter-Gene Luciferase Activity Assays

Figure 2:
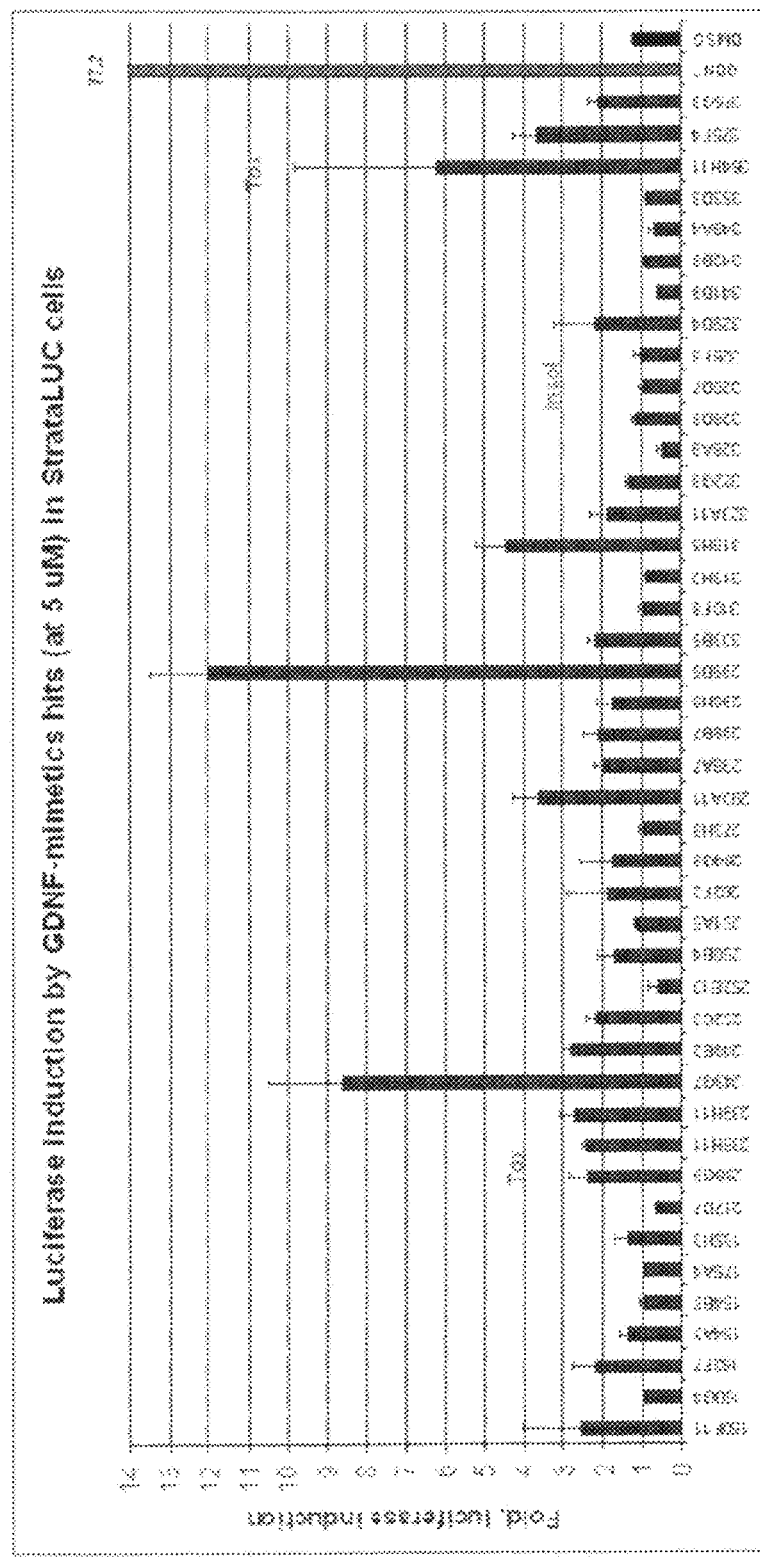

Cells were plated on 96-well plates in cell density 20 000 cells per well in DMEM, 10% FBS, 100 μg/ml Normocin, 2 μg/ml puromycin, 500 μg/ml of G418, 15 mM HEPES, pH 7.2 one day before assay. The following day, neurotrophic factors in the final concentration of 100 ng/ml were added to the wells in DMEM, 10% FBS, 100 μg/ml Normocin. Cell were allowed to produce luciferase for 24 h, than lysed in 20 μl of 1×Cell culture lysis reagent (Promega) and freeze-thawed once to ensure complete lysis. Then, 5 μl of the lysate was mixed (on ice) with 20 μl of luciferase assay substrate (Promega) in a well of black 96-well Isoplate (PerkinElmer). Luminescence was counted on MicroBeta 2 counter (PerkinElmer) twice. Results of the 2nd run were used. To optimize plating cell density 2 000-50 000 cells/well were seeded day before assay; to estimate the response of the cells stimulated with GDNF in solution, GDNF was added to the cell suspension before plating until the final concentration 10-100 ng/ml, then cells were plated on 96-well plate in the cell density 20 000 cells/well and left for 24 h to produce luciferase; for dose-response curves GFLs were added to the final concentration 5-200 ng/ml; to determine the optimal time required to produce luciferase cells were left in the culture with GDNF for 4-48 hours; to study the short-term MAPK activation, αLUC cells were treated with 100 ng/ml of GDNF for 0.5-60 min, washed once with the growth media and left in the fresh portion of growth medium for 24 hours to produce luciferase. Data are presented as M±m, where M represents an average from 4 repeats and m is standard deviation. The results of the detection are given in FIG. 2. The compounds studied included the following:

compound 299B5

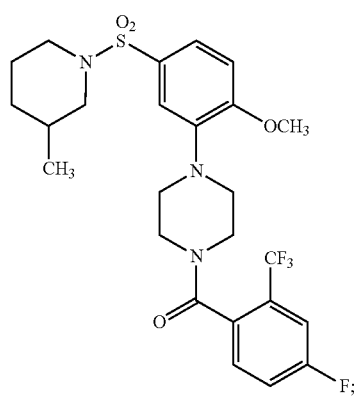

(X)

compound 290A11

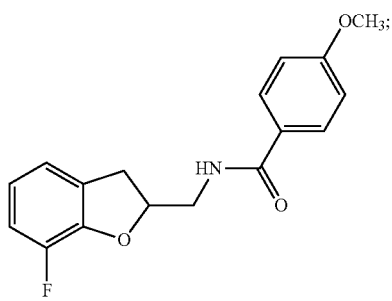 [SMILES: COc1ccc(C(=O)NCC2Cc3cccc(F)c3O2)cc1]

compound 319H6

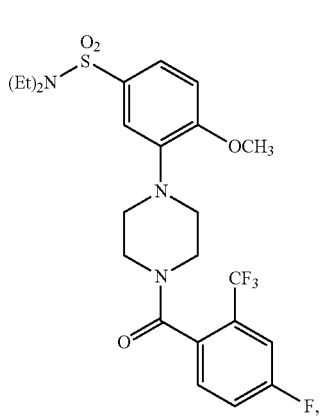

and compound 375F4

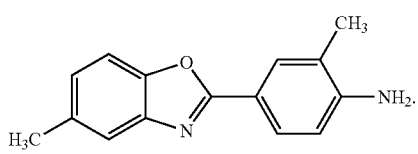

Detection of GDNF Mimetics Using Ret-ELISA Assay.

Upon stimulation with GDNF or its mimetics cells were lysed and then the lysates transferred to 96-well plate with preabsorbed anti-RET antibodies for solid-phase immunoprecipitation and subsequent phosphotyrosine detection. Preparation of the 96-well plate (OptiPlate 96 F HB, Black, Wallac) for phospho-RET detection: 1 µg/ml of goat anti-RET antibodies (Santa Cruz) were diluted in PBS. The diluted antibodies added at 75 µl/well, plate sealed and incubated overnight at +4° C. Then washed three times with PBS, 200 µl/well, blocked with Blocking solution (5% BSA in TBS) for 2 h at RT and then washed once with the Lysis buffer (TBS, 1% TritonX100, 1% NP-40, 0.25% deoxycholic acids, 10% glycerol, 1 mM $Na_3VO_4$, 1 mM EDTA, one tablet of Complete protease inhibitor (Roche) for 10 ml of the buffer). Binding of the antigen and signal detection: stimulated cells (for 5-15 min with the ligand of interest) were then placed on ice, washed once with ice-cold PBS supplemented with 1 mM sodium vanadate. After PBS removal cells were lysed in 100-200 µl of lysis buffer on ice, with shaking for at least 20 min at +4° C. The lysates at 100 µl/well were applied to the anti-RET coated 96-well plate, plate sealed and incubated 1.5-2 h on the horizontal shaker at +4° C. Then washed three times with the Washing buffer (TBS, 1% TritonX100, 2% glycerol), 200 µl/well. Anti-pY antibodies (clone 4G10, Upstate) diluted 1:1000 in Binding buffer (TBS, 1% TritonX100, 2% glycerol, 2% BSA) were added (100 µl/well) and incubate 1-1.5 h at room temperature. Then washed three times with Washing buffer, 200 µl/well. Secondary anti-mouse HRP-conjugated antibodies (Dako) at 1:3000 dilution in Binding Buffer were added at 100 µl/well. Then incubated 30-40 min at room temperature, washed three-four times with 200 µl/well of Washing buffer. Finally, 100 µl/well of pre-mixed and pre-warmed to room temperature ECL reagent. Incubated 1-2 min in dark (inside the luminometer) and counted on MicroBeta luminometer. The results of the detection are given in FIG. 3. Compound 219902 has a structure

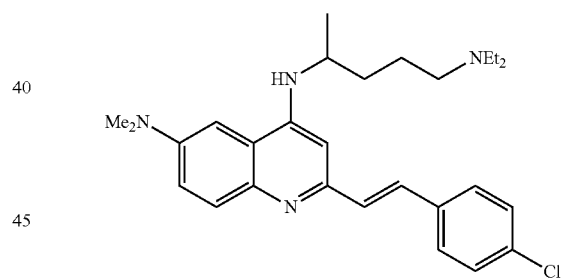

and compound 74609 has a structure

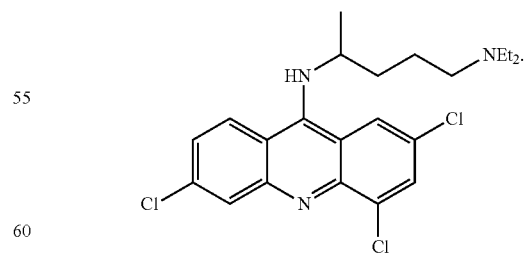

Detection of GDNF Mimetics Using Ret Phosphorylation Assay by Immunoprecipitation and Western Blotting.

αLUC and NOα cells plated on 35 mm tissue culture dishes were starved for 4 hours in serum-free DMEM and stimulated with 500 ng/ml of PSPN or 100 ng/ml of GDNF (positive control) for 15 min. Then cells were washed once with ice-cold PBS containing 1 mM Na3VO4 and lysed on ice in 1 ml per well of RIPA-modified buffer (50 mM Tris-HCl, pH 7.4, 150 mM NaCl, 1 mM EDTA, 1% NP-40, 1% TX-100, 10% glycerol, EDTA-free protease inhibitor cocktail (Roche), 1 mM Na3VO4, 2.5 mg/ml of sodium deoxycholate, 1 mM PMSF. RET was immunoprecipitated by anti-RET C-20 antibodies (Santa-Cruz Biotechnology, Inc.). Precipitated proteins were resolved on 7.5% SDS-PAGE and then transferred onto a nitrocellulose membrane. Membrane was blocked for 15 min at room temperature by 10% nonfat dry milk in TBS-T and probed with anti-phosphotyrosine antibodies (clone 4G10, Upstate Biotechnology) diluted 1:1000 in TBS-T containing 3% nonfat dry milk for 2 hours at room temperature. The membranes were washed 3 times for 5 min in TBS-T and incubated in the 1:3000 solution of secondary anti-mouse antibodies conjugated with HRP (DAKO) diluted in TBS-T containing 3% nonfat dry milk for 45 min at room temperature. Membranes were washed with TBS-T for 5×10 min. Stained bands were visualized with ECL reagent (Pierce) using LAS3000 imaging program. (FIG. 4, upper panel.) To confirm equal loading of the proteins, membranes were probed with anti-RET C-20 antibodies (1:500, Santa-Cruz Biotechnology, inc.) after stripping. We used secondary anti-goat antibodies conjugated with HRP (1:1500, DAKO) to detect C-20. The results of the detection are given in FIG. 4, lower panel.

Dose-Response of Novel (BT) GDNF- and ARTN-Mimetics Using Reporter-Gene Luciferase Activity Assays Cells were plated on 96-well plates (or 384-well) in cell density 20 000 (or 5 000 for 384-well format) cells per well in DMEM, 10% FBS, 100 µg/ml Normocin, 2 µg/ml puromycin, 500 µg/ml of G418, 15 mM HEPES, pH 7.2 one day before assay. The following day, the compounds were added to a final concentration of 1-50 µM. Structures of the compounds are shown in the description of FIG. 5, above. Cells were allowed to produce luciferase for 24 h, then lysed in 20 µl of 1×Cell culture lysis reagent (Promega) and freeze-thawed once to ensure complete lysis. Then 5 µl of the lysate was mixed (on ice) with 20 µl of luciferase assay substrate (Promega) in a well of black Isoplate (PerkinElmer). Luminescence was counted on MicroBeta 2 counter (PerkinElmer) twice. Data are presented as fold induction, where the corresponding concentration of DMSO was used as a reference. See FIG. 5 for data.

Activity of Novel (BT) GDNF-/ARTN-Mimetics in Ret Phosphorylation Assay by Immunoprecipitation and Western Blotting.

MG87RET cells were plated on 35 mm tissue culture dishes the day before the experiment. Cells were transfected with GFRα1, GFRα3 or with an vector encoding for GFP. On the day of the experiment cells were starved for 4 hours in serum-free DMEM and stimulated with the investigated compounds (structures shown in the description of FIG. 6, above) at 100 µM concentration or with 100 ng/ml of GDNF or ARTN (positive control) for 15 min. Then cells were washed once with ice-cold PBS containing 1 mM $Na_3VO_4$ and lysed on ice in 1 ml per well of RIPA-modified buffer (50 mM Tris-HCl, pH 7.4, 150 mM NaCl, 1 mM EDTA, 1% NP-40, 1% TX-100, 10% glycerol, EDTA-free protease inhibitor cocktail (Roche), 1 mM Na3VO4, 2.5 mg/ml of sodium deoxycholate, 1 mM PMSF. Ret was immunoprecipitated by anti-RET C-20 antibodies (Santa-Cruz Biotechnology, Inc.). Precipitated proteins were resolved on 7.5% SDS-PAGE and then transferred onto a nitrocellulose membrane. Membrane was blocked for 15 min at room temperature by 10% nonfat dry milk in TBS-T and probed with anti-phosphotyrosine antibodies (clone 4G10, Upstate Biotechnology) diluted 1:1000 in TBS-T containing 3% nonfat dry milk for 2 hours at room temperature. The membranes were washed 3 times for 5 min in TBS-T and incubated in the 1:3000 solution of secondary anti-mouse antibodies conjugated with HRP (DAKO) diluted in TBS-T containing 3% nonfat dry milk for 45 min at room temperature. Membranes were washed with TBS-T for 5×10 min. Stained bands were visualized with ECL reagent (Pierce) using LAS3000 imaging program. To confirm equal loading of the proteins, membranes were probed with anti-RET C-20 antibodies (1:500, Santa-Cruz Biotechnology, inc.) after stripping. We used secondary anti-goat antibodies conjugated with HRP (1:1500, DAKO) to detect C-20. The results are shown in FIG. 6.

Parkinson's Disease Animal Model

All rats are exposed to a i.p. injections of active compounds (i.e. GFL-mimetics or RET-signaling activators) and/or to stereotaxic microinfusion twice; first rats are given either vehicle (4 µl), active compounds (1-100 mg/kg) or GDNF (10 µg) and 6 hours later each animal receives 6-OHDA (8 µg) to the same site in left dorsal Striatum. The coordinates in the left striatum relative to the bregma and dura are A/P+1.0, LJM+2.7, D/V-4 according to the atlas of Paxinos and Watson (Paxinos and Watson, 1997, The rat brain in stereotaxic coordinates, Academic press, San Diego). The study consisted of following groups: intra striatal PBS+6-OHDA, intra striatal GDNF+6-OHDA and intrastriatal GFL-mimetics+6-OHDA, intra striatal PBS+6-OHDA+i.p. GFL-mimetics.

Rotational Behavior:

Behavioral tests are carried out 2 and 4 weeks postlesion. The rats are allowed to habituate to the test chamber for 30 min before D-amphetamine (University Pharmacy, Helsinki, Finland; 2.5 mg/kg i.p) is administrated. The number of full (360°) ipsilateral and contralateral turns is recorded for a period of 2 h. Net ipsilateral turns to the lesion is calculated by subtracting the turns to the left from the turns to the right.

Immunohistochemistry:

At 4 weeks postlesion, the rats are anesthetized with an overdose of natriumpentobarbital (90 mg/kg, i.p, Orion Pharma, Finland) and perfused intracardially with phosphate-buffered saline (PBS) followed by 4% paraformaldehyde in 0.1 M sodium phosphate buffer, pH 7.4. The brains are removed, postfixed for 4 h and stored in sodium phosphate buffer containing 20% sucrose at 4° C. Serial coronal cryo-sections of 40 µm are cut on a sliding microtome. Six sets of sections are collected in cryoprotectant solution (0.5M PB, 30% glycerol and 30% ethylenglycole) and stored at −20° C. until immunohistochemical processing. Free-floating sections are processed for TH-immunohistochemistry. Following three rinses in PBS, endogenous peroxidase activity is quenched in 3% $H_2O_2$/10% methanol/PBS for 5 minutes. After 3 rinses in PBS, sections are preincubated with normal horse serum (NHS)/0.3% Triton X-100 in PBS in order to block nonspecific staining. Thereafter, sections are incubated overnight at room temperature with 1:2000 dilution of biotinylated mouse-anti-TH (Chemic on, Temecula, Calif.). Then, the sections are incubated with 1:200 dilution of biotinylated horse-anti-mouse (Vector, BA2001) and by incubation in the avidin-biotin peroxidase complex using the Elite ABC Vectastain kit (Vector Laboratories). The reactions are visualized using DAB as a chromogen.

Morphological Analysis/SN Cell Counts:

Unbiased stereological cell counting procedures are used to count TH-positive cells in the substantia nigra pars compacta (SNpc) by using the optical fractionator method in combination with the dissector principle and unbiased counting rules (West et al., 1991, Anat. Rec. 231, 482-497; Mouton et al., 2002, Brain Res. 956, 30-35). The entire SNpc is analyzed with Stereo Investigator platform (MicroBrightField, Germany) attached to Olympus BX51 microscope. From each animal, 3 sections from the central portion of the SNpc, where the medial terminal nucleus (MTN) is present (level A/P−5.3), are selected for quantitative analysis. Optical fractionator estimation method is optimized to give coefficient of error less than x % per individual brain sample. Each reference space is outlined at low power (4×), and cells are counted using a high magnification (60×, oil immersion) objective.

In male Wistar rats, a single injection of active compounds into Striatum and/or i.p. prevents the 6-hydroxydopamine (6-OHDA, 8 μg) induced degeneration of dopaminergic nerves of the Nigro-Striatal tract. Under anesthesia, the rats are exposed to a stereotaxic microinjection twice. First, they are given either vehicle (PBS, 4 μl, the control group) or active compounds and 6 hours later each animal receives 6-OHDA (8 μg) to the same site in left dorsal Striatum. The coordinates in the left striatum relative to the bregma and dura are A/P+1.0, L/M+2.7, D/V-4 according to the atlas of Paxinos and Watson (Paxinos and Watson, 1997, The rat brain in stereotaxic coordinates, Academic press, San Diego).

Behavioral tests are carried out twice in all rats. Two and 4 weeks post lesion each rat is given D-amphetamine (2.5 mg/kg, i.p.) in order to induce ipsilateral (to the side of lesion) turning behavior, which is recorded for a period of 2 h. At two weeks post lesion, it is expected that amphetamine (2.5 mg/kg, i.p.) induces significant ipsilateral turning behavior in the control group. On the contrary, it is expected that minimum or no increase in ipsilateral turns is observed in the treatment group (treated with active compounds prior to 6OHDA). At four weeks post-lesion, it is expected that active compounds are able to significantly reverse the amphetamine induced ipsilateral turning, and the immunohistochemical analysis shows significant protection of DAergic cells by the neurotrophic factor.

TH-immunohistochemistry. At 4 weeks post lesion, following the second behavioral experiment, the rats are anesthetized with an overdose of sodium pentobarbital (90 mg/kg) and perfused intracardially with phosphate-buffered saline (PBS) followed by 4% paraformaldehyde in 0.1 M sodium phosphate buffer, pH 7.4. Freefloating sections will be processed for TH-immunohistochemistry. Unbiased stereological cell counting procedures is used to count TH-positive cells in the substantia nigra pars compacta (SNpc) by using the optical fractionator method in combination with the dissector principle and unbiased counting rules (West et al. 1991, Anat. Rec. 231, 482-497; Mouton et al. 2002, Brain Res. 956, 30-35). The entire SNpc is analyzed with Stereo Investigator platform (MicroBrightField, Germany) attached to Olympus BX51 microscope. The loss of TH positive cells in Substantia Nigra pars compacta of control group and treatment group is expected to be about 30% and about 4%, respectively.

Another Parkinson's Disease Study

The objective of this study is to investigate the effect of intrastriatally (i.s.) administered small molecule GDNF mimetics (compounds 13, 16, 319H6 and 292651, structures shown in the description of the Figures, above) in a rat model 6-OHDA of Parkinson's disease. In the sub-acute lesion model used in this study, the lesion of the substantia nigra (SNc) that slowly progresses over weeks is created by injection of 6-OHDA into the proximity of the dopaminergic terminals in the striatum (Kirik-D 1998, Exp. Neurol. 152:259-277). In this model, a portion of the nigrostriatal projection is left intact, which can serve as a substrate for regeneration and functional recovery in response to growth promoting and neuroprotective agents.

GDNF mimetics compounds, GDNF or vehicle is administered to the striatum at 3 weeks after the exposure to the neurotoxin 6-OHDA. The selective damage to dopaminergic neurons in the SNc, as well as striatal levels of dopamine and its metabolites are evaluated 12 weeks after the injection of 6-OHDA with tyrosine hydroxylase (TH) immunohistochemistry and HPLC, respectively. In addition, the behavioral impairment of rats is evaluated by forelimb asymmetry test (cylinder test), amphetamine induced rotation asymmetry test and Y-maze test for stereotypic spontaneous rotation deficits.

Animals: All animal experiments are carried out according to the National Institute of Health (NIH) guidelines for the care and use of laboratory animals, and approved by the State Provincial Office of Southern Finland. Altogether 108 male Wistar rats, purchased from Charles River, Germany and weighing 220-275 g are used for the experiment. Animals are housed at a standard temperature (22±1° C.) and in a light-controlled environment (lights on from 7 am to 8 pm) with ad libitum access to food and water. Animals are grouped as follows:

Group 1: 12 rats treated with Vehicle (0 mg/kg, i.s.) at 3 weeks after 6-OHDA infusion
Group 2: 12 rats treated with BT13 (5 ug per rat i.e. 0.4 mg/kg, i.s.) at 3 weeks after 6-OHDA infusion
Group 3: 12 rats treated with BT13 (1 ug per rat i.e. 0.1 mg/kg, i.s.) at 3 weeks after 6-OHDA infusion
Group 4: 12 rats treated with BT13 (0.2 ug per rat i.e. 0.2 mg/kg, i.s.) at 3 weeks after 6-OHDA infusion
Group 5: 12 rats treated with BT16 (0.5 ug per rat i.e. 0.2 mg/kg, i.s.) at 3 weeks after 6-OHDA infusion
Group 6: 12 rats treated with BT292651 (5 ug per rat i.e. 0.4 mg/kg, i.s.) at 3 weeks after 6-OHDA infusion
Group 7: 12 rats treated with BT292651 (1 ug per rat i.e. 0.1 mg/kg, i.s.) at 3 weeks after 6-OHDA infusion
Group 8: 12 rats treated with BT18 (1 ug per rat i.e. 0.2 mg/kg, i.s.) at 3 weeks after 6-OHDA infusion
Group 9: 12 rats treated with GDNF (R&D Systems, Ltd.; 10 ug per rat, or about 40 ug/kg, i.s.) at 3 weeks after 6-OHDA infusion In order to generate partial retrograde degeneration into the SNc, 6-OHDA lesioning is carried out according to Sauer and Oertel with modifications (Sauer and Oertel, 1994). Male Wistar rats are anesthetized with 5% isoflurane (in 70% $N_2O$ and 30% $O_2$; flow 300 ml/min) and placed in a stereotactic frame. During the operation concentration of anesthetic is reduced to 1-1.5%. The rectal temperature is maintained at 37.0±1.0° C. with a homeothermic blanket system. The right brain hemisphere is exposed through a small craniectomy to the skull. The dura mater is carefully removed with fine forceps and a stereotaxic injection of 6-OHDA (4 μg/μl) is made into the right striatum. A total of 7 μl of 6-OHDA is infused at a speed of 0.5 μl/min and is equally distributed between 4 sites at the following coordinates: AP+1.0, ML+2.8, DV−6.0, −5.5, −5.0 and −4.4 mm. The cannula is left in place for another 5 min before being withdrawn. The hole in the skull is subsequently filled with repair material and the skin is closed and disinfected. The rats are allowed to recover from anesthesia and are carefully monitored for possible post surgical complications. The animals are returned to the home cages with ad libitum access to food and water.

On day 21, rats are re-anesthetized with 5% isoflurane (in 70% $N_2O$ and 30% $O_2$; flow 300 ml/min) and placed in a stereotactic frame. During the operation concentration of anesthetic is reduced to 1-1.5%. The rectal temperature is maintained at 37.0±1.0° C. with a homeothermic blanket system. The right brain hemisphere is exposed through a small craniectomy to the skull. A stereotaxic injection of the test compound, GDNF or vehicle is made into the right striatum. Each dosing solution is infused at a speed of 1 µl/min and is equally distributed between 4 sites at the following coordinates: AP+1.0, ML+2.8, DV−6.0, −5.5, −5.0 and −4.4 mm. The cannula is left in place for another 5 min before being withdrawn. The hole in the skull is subsequently filled with repair material and the skin is closed and disinfected. The rats are allowed to recover from anesthesia and are carefully monitored for possible post surgical complications. The animals are returned to the home cages with ad libitum access to food and water.

Behavioral Testing:

Forelimb Use and Preference in Spontaneous Rearing—Cylinder Test The cylinder test (modified from Schallert and Tillerson in Innovative models of CNS disease: from molecule to therapy. Clifton, N.J., Humana, 1999) is used to quantify the forelimb use for spontaneous rearing on the home cage wall. The test is performed on days 14, 35, 56 and 77 days after the 6-OHDA injection. The rats are monitored as they move freely in their home cage. Contacts made by each forepaw with the cage wall while rearing are scored by a blinded observer to the treatment. A total of 20 contacts are recorded for each animal, and the number of impaired and non-impaired forelimb contacts as percentage of total contacts is calculated.

Y-maze Test for Spontaneous Turning Preference and Activity

The Y-maze is made of black painted plastic. Each arm of the Y-maze is 35 cm long, 25 cm high and 10 cm wide and positioned at an equal angle. 14, 35, 56 and 77 days after 6-OHDA lesioning, each rat is placed at the end of one arm and allowed to move freely through the maze for an 8-min session. The sequence of arm entries is recorded manually. Rats with unilateral 6-OHDA lesion tend to turn away from the side of higher dopamine activity (unlesioned, left) and therefore show bias for right turnings. The percentage of right turning preference is determined from the data set as the percentage of right turns over all turns ((right/left+right)×100%). In addition to right turning preference scores, total number of arm entries is measured.

Amphetamine Induced Rotation Asymmetry

The animals are tested for amphetamine-induced rotation behavior on days 42 and 84 days after the 6-OHDA injection. Motor asymmetry is monitored in automated rotometer bowls (TSE Systems, Germany) for 45 min after injection of amphetamine (5 mg/kg i.p.). The net ipsiversive rotation asymmetry score for each test is calculated by subtracting contralateral turns from the ipsilateral turns to the lesion.

General Health Status and Humane End-Points

Animals are monitored daily by laboratory personnel. In the case that the general health status of an animal has significantly worsened, the rat is terminated by an overdose of $CO_2$, and decapitated. Definitions of acceptable endpoints include: no spontaneous movements and inability to drink or eat in 24-h observation period, massive bleeding, spontaneous inflammation, missing anatomy, swelling or tumors larger than 20 mm, and inability to right itself in 30 sec period.

Eighty-five days after the 6-OHDA exposure, animals are transcardially perfused with heparinized (2.5 IU/ml) saline in order to remove blood from the brains. Thereafter the brains are removed and dissected on ice.

Ipsi- and contralateral striatum is dissected out in toto, weighed, snap-frozen on dry ice, and stored at −80° C. for the HPLC analysis of dopamine and its metabolites. All ipsilateral striatum samples are subjected to HPLC analysis. Contralateral samples are not subjected to HPLC analysis.

The posterior brain block containing the SNc is fixed by immersion in 4% paraformaldehyde in 0.1 M phosphate buffer (PB) for 24 hours. Following cryoprotection in 30% sucrose in 0.1M PB for 2-3 days and freezing the blocks in liquid nitrogen, 20-µm-thick cryosections are prepared with a cryostat. From each rat 4 sections in one Superfrost™ glass slide (sections 100 µm apart) are used for TH immunohistochemistry (4 extra glass slides each containing 4 sections are also collected and stored in −80° C. as spare samples). The sections are first re-hydrated and then permeabilized in PBS containing 0.5% Tween-20. The sections are blocked in 5% goat serum in PBST (PBS with 0.05% Tween 20), followed by overnight incubation with 1:1500 rabbit anti-TH (Novus Biologicals cat# NB300-109) polyclonal antibody at RT. Thereafter the sections are washed, and incubated with Alexa Fluor® 594 conjugated goat anti-rabbit IgG secondary antibody (Molecular Probes cat# A11012) for 2 h at RT. Finally, the sections are rinsed, dehydrated, coverslipped and examined with Olympus AX-70 fluorescence microscope. The number of TH-immunofluorescent neurons is counted through the SNc (4 sections per animal).

Ipsilateral striata are subjected to HPLC. Dopamine (DA), 3,4-dihydroxyphenylacetic acid (DOPAC) and homovanillic acid (HVA) concentrations in striatal tissue samples are determined by high performance liquid chromatography (HPLC) method with electrochemical detection.

After thawing on ice, tissue samples are homogenized (1:10, w/v) in 0.1 M perchloric acid with MSE Soniprep 150 ultrasonic disintegrator (MSE Scientific Instruments, Crawley, UK). Tissue homogenates are centrifuged for 15 min at 15000 g at 4° C. Supernatants are filtered through polypropylene membrane (GHP Acrodisc 13 0.45 um, Pall Corporation, Ann Arbor, Mich., USA) and diluted (1:1) with 0.1 M perchloric acid. The samples are transferred into plastic vials and analyzed immediately.

The ESA HPLC system (ESA Inc., Chelmsford, Mass., USA) consists of a 582 solvent delivery system, a DG-1210 vacuum degasser, an 542 autosampler, a 880 thermostatted chamber, an eight-channel CoulArray® 5600 electrochemical array detector equipped with a two-channel 5014B microdialysis cell and a CoulArray® for Windows data acquisition module (version 1.00). The applied potentials are −175 mV (channel 1), +225 mV (channel 2), +350 mV (channel 3) and +450 mV (channel 4). DA and DOPAC are detected on channel 2 and HVA on channel 3. Injection volume is 10

The analytes are separated on a Zorbax SB-Aq reversed-phase column (2.1×100 mm, 3.5 µm, Agilent Technologies Inc., Little Falls, Wilmington, Del., USA) with a Zorbax SB-Aq precolumn (2.1×12.5 mm, 5 µm) in an isocratic run. The column is maintained at 35° C. The mobile phase is 100 mM monobasic sodium phosphate containing 4.75 mM citric acid monohydrate, 7 mM 1-octanesulfonic acid and 50 µM disodium EDTA-acetonitrile mixture (98:2, v/v). The pH of the mobile phase is adjusted to 2.2 with o-phosphoric acid. The flow, rate is 0.3 ml/min. The levels of DA, DOPAC and HVA are expressed as nmol/g wet tissue.

All values are presented as mean±standard deviation (SD) or standard error of mean (SEM), and differences are considered to be statistically significant at the $P<0.05$ level. Statistical analysis is performed using StatsDirect statistical software. Differences among means are analyzed by using 1-way-ANOVA followed by Dunnet's test (comparison to the control (=vehicle treated rats) group). Non-parametric data is analyzed with Kruskal-Wallis ANOVA.

Results:

Animals have been followed for 12 weeks and GDNF mimetics compounds that were injected into the striatum of 6-OHDA-treated rats did not induce side effects. In behavioral assays it was also evident that compounds BT13, BT16, BT18 and BT292651 when injected intrastriatally did not cause toxic effects.

In the amphetamine induced rotation assay carried out 6 weeks after 6-OHDA injection and 3 weeks after intrastriatal injection of the compounds BT13 (or 13), BT16 (or 16), BT18 (or 18) and BT292651 (or 292651) compounds; BT13 at one concentration (0.2 ug), compound BT16, BT18 and compound BT292651 also at one concentration (1 ug) reduced amphetamine-induced ipsilateral rotation. See FIG. 7.

GDNF mimetics compounds BT13, BT16, BT18 and BT292651 when injected 3 weeks after the injection to 6-OHDA neurotoxin into the striatum significantly reduce amphetamine-induced ipsilateral rotation of lesioned rats. Thus, compounds BT13, BT16, BT18 and BT292651 significantly reduce pathological motoric movement in rat model of Parkinson's disease in vivo.

Dopaminergic Neuron Survival

Rat dopaminergic neurons were cultured as described by Schinelli et al., 1988. Briefly pregnant female rats of 15 days gestation were killed by cervical dislocation (Rats Wistar; Janvier) and the fetuses removed from the uterus. The embryonic midbrains were removed and placed in ice-cold medium of Leibovitz (L15; Invitrogen) containing 1% of Penicillin-Streptomycin (PS; Invitrogen) and 1% of bovine serum albumin (BSA; Sigma). Only the ventral portions of the mesencephalic flexure were used for the cell preparations as this is the region of the developing brain rich in dopaminergic neurons.

The midbrains were dissociated by trypsinisation for 20 min at 37° C. (10% of trypsin EDTA 10×; Invitrogen) diluted in PBS without calcium and magnesium. The reaction was stopped by the addition of Dulbecco's modified Eagle's medium (DMEM; Invitrogen) containing DNAase I grade II (0.1 mg/ml; Roche Diagnostic;) and 10% of fetal calf serum (FCS; Invitrogen). Cells were then mechanically dissociated by 3 passages through a 10 ml pipette. Cells were then centrifuged at 180×g for 10 min at room temperature on a layer of BSA (3.5%) in L15 medium. The supernatant was discarded and the cells of pellet were re-suspended in a defined culture medium consisting of Neurobasal (Invitrogen) supplemented with B27 (2%; Invitrogen), L-glutamine (0.2 mM; Invitrogen) and 1% of PS solution. Viable cells were counted in a Neubauer cytometer using the trypan blue exclusion test.

The cells were seeded at a density of 69 000 cells/well in 96 well-plates (wells were pre-coated with poly-L-lysine (10 μg/ml; Sigma)) and were cultured at 37° C. in a humidified air (95%)/$CO_2$ (5%) atmosphere. Half of the medium was changed every 2 days with fresh medium. In these conditions, after 5 days of culture, astrocytes were present in the culture and release growth factor allowing neurons differentiation. Three to five percent of the neuronal cell population were dopaminergic neurons.

On day 6, the medium was removed and fresh medium was added with or without $MPP^+$ at 16 μM and with or without test substance. After 48 hours of intoxication (day 8 of culture), the cells were fixed with PFA 4%. Dopaminergic neurons were labeled by a monoclonal anti-tyrosine hydroxylase (TH) antibody (Sigma). This antibody labels the neurites and cell bodies of dopaminergic neurons. This antibody was revealed with Alexa Fluor 488 goat anti-mouse IgG (Molecular probe) and the nuclei of the cells were labeled by a fluorescent marker (Hoechst solution, SIGMA). For each condition, 2×10 pictures per well were taken using InCell Analyzer™ 1000 (Amersham Biosciences) with 10× magnification. All the images were taken in the same conditions.

Analysis of the neurite length and number of neurons labeled with anti tyrosine hydroxylase (TH) antibodies with or without MPP+ intoxication was carried out using InCell Analyzer™ 1000 3.2.Workstation software. Dopaminergic neurons and total length neurites were counted on the 10 pictures (12 analyses by culture condition).

The cytoprotection by the compound 319H6 is demonstrated by the data in the Table below. These results clearly demonstrate that the neuroprotective effect of the compound is similar to the native brain-derived neurotrophic factor (BDNF).

TABLE

| Treatment | Dose (μM) | % $TH^+$ Neurons | % Cytoprotection vs controls |
|---|---|---|---|
| DMSO | 0 | 55 | 0 |
| 319H6 | 0.1 | 59 | 9 |
| 319H6 | 1 | 70 | 33 |
| 319H6 | 10 | 71 | 36 |
| BDNF* | 10 | 77 | 49 |

*BDNF concentration is in ng/mL

Assessment of GDNF=/ARTN-Mimetics on Cell Viability

The test compounds were transferred into in 384-well culture plate using Echo acoustic dispenser (Labcyte Inc.) in 2.5-125 nl volume. Trypsinized MG87RET murine fibroblasts were seeded at 20 000 cells/ml (500 cells/well) in the presence of each compound dissolved in DMSO at the indicated concentration. After brief mixing on a horizontal shaker, the plates were centrifuged and transferred into the incubator. Two days (48 hours) after addition of cells to compounds, the viability of the cells was evaluated using CelTiterGlo reagent (Promega). The results are shown in FIG. 8.

Amphetamine-Induced Rotation

Rats received vehicle, GDNF, or a GDNF mimetic in the striatum three weeks after a lesion was induced by intrastriatal 6-OHDA. Amphetamine-induced behavior was measured for at 42 and 84 days after the lesion. Motor asymmetry was monitored in automated rotometer bowls (TSE Systems, Germany) for 45 min after injection of amphetamine (5 mg/kg i.p.). The net ipsiversive rotation asymmetry score for each test was calculated by subtracting contralateral turns from the ipsilateral turns to the lesion. Data are shown in FIG. 9, below.

Other Relevant Diseases Models

Similar to experiments described above for Parkinson's disease, experiments are designed and conducted for relevant disease models: ALS (e.g. SOD1G93A rat model), cerebral ischemia (e.g. middle cerebral artery ligation rodent model), Alzheimer's disease (e.g., Aβ-overexpressing transgenic mouse model), chronic pain (e.g. spinal nerve ligation rat model) and others.

REFERENCES

The documents cited herein are incorporated by reference in their entirety. In addition, where documents are cited for their teachings of specific assays or reagents, these specific teachings are incorporated by reference.

Airaksinen, and Saarma. 2002. The GDNF family: signalling, biological functions and therapeutic value. Nat Rev Neurosci. 3:383-94.

Airavaara, et al. 2004. Increased extracellular dopamine concentrations and FosB/DeltaFosB expression in striatal brain areas of heterozygous GDNF knockout mice. Eur J. Neurosci. 20:2336-44.

Baloh, et al. 2000. Functional mapping of receptor specificity domains of glial cell line-derived neurotrophic factor (GDNF) family ligands and production of GFRα1 RET-specific agonists. J Biol. Chem. 275:3412-20.

Bespalov and Saarma. 2007. GDNF family receptor complexes are emerging drug targets. Trends Pharmacol Sci. 28:68-74.

Enslen, et al. 1996. Regulation of mitogen-activated protein kinases by a calcium/calmodulin-dependent protein kinase cascade. Proceedings of the National Academy of Sciences of the United States of America. 93:10803.

Garces, et al. 2001. Responsiveness to neurturin of subpopulations of embryonic rat spinal motoneuron does not correlate with expression of GFRα1 or GFRα2. Dev Dyn. 220:189-97.

Gardell, et al. 2003. Multiple actions of systemic artemin in experimental neuropathy. Nat. Med. 9:1383-9.

Gill, et al. 2003. Direct brain infusion of glial cell line-derived neurotrophic factor in Parkinson disease. Nat. Med. 9:589-95.

Golden, et al. 2003. Neurturin and persephin promote the survival of embryonic basal forebrain cholinergic neurons in vitro. Exp Neurol. 184:447-55.

He, et al. 2005. Glial cell line-derived neurotrophic factor mediates the desirable actions of the anti-addiction drug ibogaine against alcohol consumption. J. Neurosci. 25:619-28.

Henderson, et al. 1994. GDNF: a potent survival factor for motoneurons present in peripheral nerve and muscle. Science. 266:1062-4.

Katritzky, et al. 2008. Novel computational models for predicting dopamine interactions. Experimental Neurology. 211:150-171.

Knowles, et al. 2006. Structure and chemical inhibition of the RET tyrosine kinase domain. J Biol. Chem. 281:33577-87.

Lang, et al. 2006. Randomized controlled trial of intraputamenal glial cell line-derived neurotrophic factor infusion in Parkinson disease. Ann Neurol. 59:459-66.

Leppänen, et al. 2004. The structure of GFRα1 domain 3 reveals new insights into GDNF binding and RET activation. EMBO J. 23:1452-62.

Lin, et al. 1993. GDNF: a glial cell line-derived neurotrophic factor for midbrain dopaminergic neurons. Science. 260:1130-2.

Lindholm, et al. 2007. Novel neurotrophic factor CDNF protects and rescues midbrain dopamine neurons in vivo. Nature. 448:73-7.

Longo, et al., Methods of facilitating neural cell survival using non-peptide and peptide BDNF neurotrophin mimetics, US Patent Appl. 20070060526, Mar. 15, 2007.

Marais, et al. 1993. The SRF accessory protein Elk-1 contains a growth factor regulated transcriptional activation domain. Cell. 73:381-93.

Marks, et al. 2008. Safety and tolerability of intraputaminal delivery of CERE-120 (adeno-associated virus serotype 2-neurturin) to patients with idiopathic Parkinson's disease: an open-label, phase I trial. Lancet Neurol. 7:400-8.

Meng, et al. 2001. Promotion of seminomatous tumors by targeted overexpression of glial cell line-derived neurotrophic factor in mouse testis. Cancer Res. 61:3267-71.

Meng, et al. 2000. Regulation of cell fate decision of undifferentiated spermatogonia by GDNF. Science. 287:1489-93.

Messer, et al. 2000. Role for GDNF in biochemical and behavioral adaptations to drugs of abuse. Neuron. 26:247-57.

Mijatovic, et al. 2007. Constitutive Ret activity in knock-in multiple endocrine neoplasia type B mice induces profound elevation of brain dopamine concentration via enhanced synthesis and increases the number of TH-positive cells in the substantia nigra. J. Neurosci. 27:4799-809.

Parkash, et al. 2008. The structure of the glial cell line-derived neurotrophic factor coreceptor complex: insights into RET signaling and heparin binding. J Biol. Chem. 283:35164-72.

Pichel, et al. 1996. Defects in enteric innervation and kidney development in mice lacking GDNF. Nature. 382:73-6.

Runeberg-Roos, et al. 2007. RET(MEN 2B) is active in the endoplasmic reticulum before reaching the cell surface. Oncogene. 26:7909-7915.

Santoro, et al. 2004. Minireview: RET: normal and abnormal functions. Endocrinology. 145:5448-51.

Sariola and Saarma. 2003. Novel functions and signalling pathways for GDNF. J Cell Sci. 116:3855-62.

Sauer H & Oertel W H (1994) Progressive degeneration of nigrostriatal dopamine neurons following intrastriatal terminal lesions with 6-hydroxydopamine: a combined retrograde tracing and immunocytochemical study in the rat. Neuroscience, 59(2):401-15.

Sautter, et al. 1998. Implants of polymer-encapsulated genetically modified cells releasing glial cell line-derived neurotrophic factor improve survival, growth, and function of fetal dopaminergic grafts. Exp Neurol. 149:230-6.

Schinelli S, Zuddas A, Kopin L I, Barker J L, di Porzio U (1988) 1-Methyl-4-phenyl-1,2,3,6-tetrahydropyridine metabolism and 1-methyl-4-phenylpyridinium uptake in dissociated cell cultures from the embryonic mesencephalon. J Neurochem, 50(6):1900-7.

Sild, et al. 2006. Open computing grid for molecular science and engineering. J Chem Inf Model. 46:953-9.

Slevin, et al. 2005. Improvement of bilateral motor functions in patients with Parkinson disease through the unilateral intraputaminal infusion of glial cell line-derived neurotrophic factor. J. Neurosurg. 102:216-22.

Tokugawa, et al. 2003. XIB4035, a novel nonpeptidyl small molecule agonist for GFRα-1. Neurochem Int. 42:81-6.

Tomac, et al. 2002. Effects of cerebral ischemia in mice deficient in Persephin. Proc Natl Acad Sci USA. 99:9521-6.

Tovar, et al. 2007. Comparison of 2D Fingerprint Methods for Multiple-Template Similarity Searching on Compound Activity Classes of Increasing Structural Diversity. ChemMedChem. 2:208-217.

Wang, et al. 2006. Structure of artemin complexed with its receptor GFRα3: convergent recognition of glial cell line-derived neurotrophic factors. Structure. 14:1083-92.

Wang, et al. 2008. Persistent restoration of sensory function by immediate or delayed systemic artemin after dorsal root injury. Nat. Neurosci. 11:488-96.

The invention claimed is:

1. A compound having a structure selected from the group consisting of

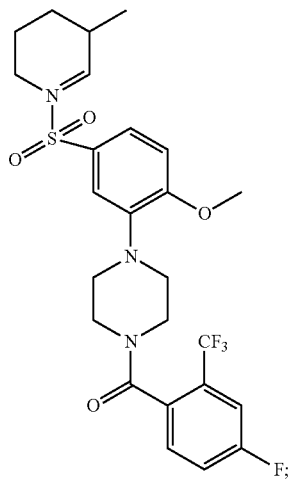
(VI)

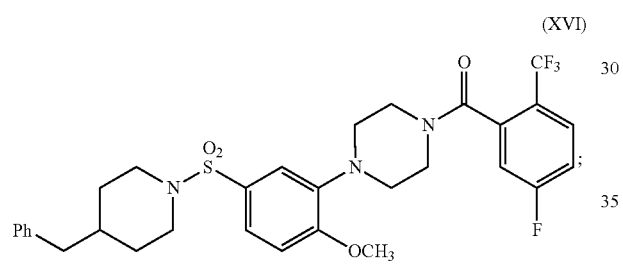
(XVI)

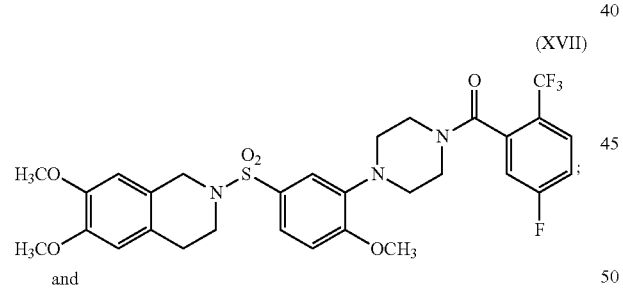
(XVII)
and

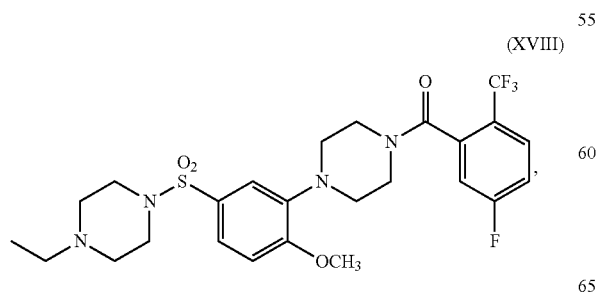
(XVIII)

or a pharmaceutically acceptable salt thereof.

2. The compound of claim 1, having a structure

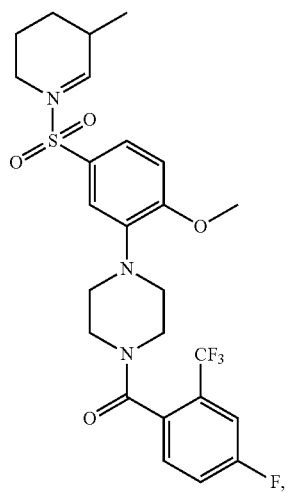
(VI)

or pharmaceutically acceptable salt thereof.

3. The compound of claim 1, having a structure

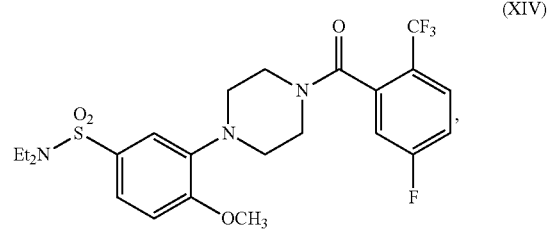
(XIV)

or pharmaceutically acceptable salt thereof.

4. The compound of claim 1, having a structure

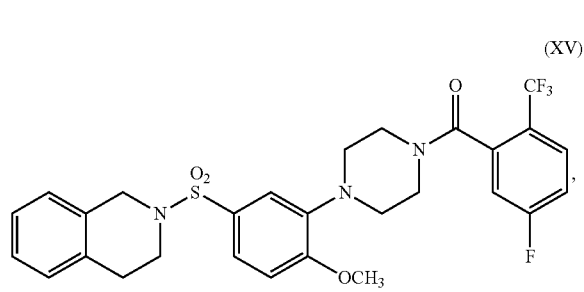 [SMILES: COc1ccc(S(=O)(=O)N2CCc3ccccc3C2)cc1N1CCN(C(=O)c2cc(F)ccc2C(F)(F)F)CC1]
(XV)

or pharmaceutically acceptable salt thereof.

5. The compound of claim 1, having a structure

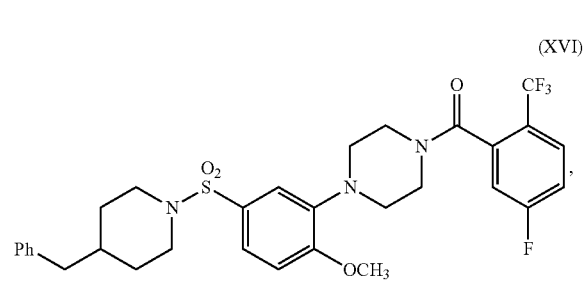 [SMILES: COc1ccc(S(=O)(=O)N2CCC(Cc3ccccc3)CC2)cc1N1CCN(C(=O)c2cc(F)ccc2C(F)(F)F)CC1]
(XVI)

or pharmaceutically acceptable salt thereof.

6. The compound of claim 1, having a structure

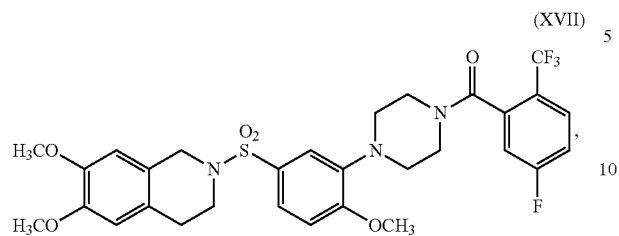
(XVII)

or pharmaceutically acceptable salt thereof.

7. The compound of claim 1, having a structure

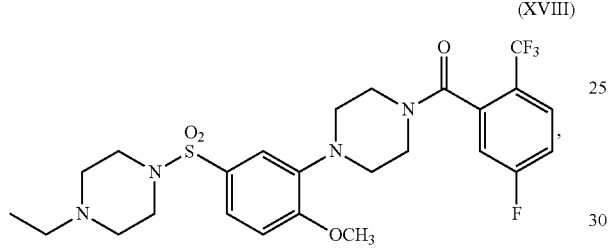
(XVIII)

or pharmaceutically acceptable salt thereof.

8. A method of treating Parkinson's disease in a subject in need thereof, comprising administering a therapeutically effective amount of the compound of claim 1 to the subject.

9. A method of treating Parkinson's disease in a subject in need thereof, comprising administering to the subject a therapeutically effective amount of a compound selected from the group consisting of:

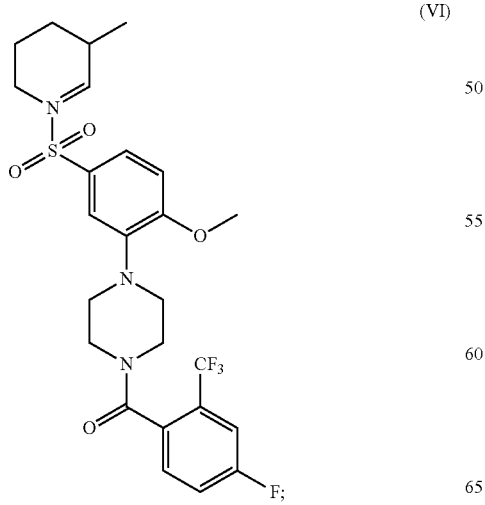
(VI)

-continued

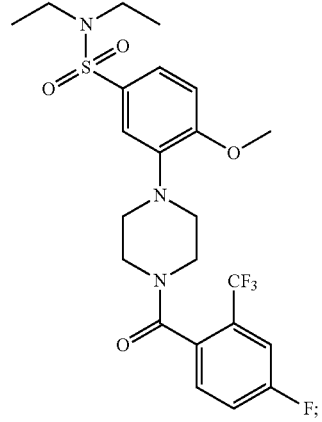
(VII)

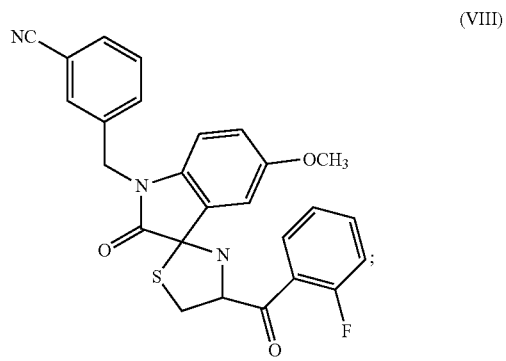
(VIII)

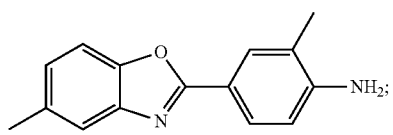
(IX)

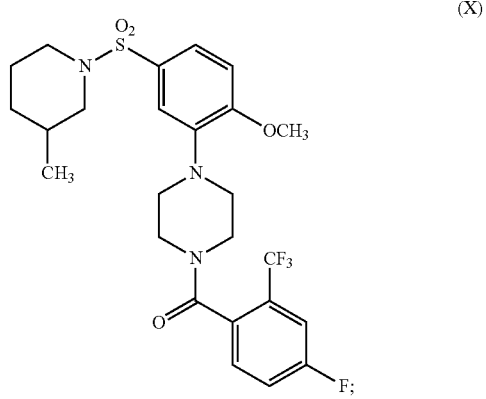
(X)

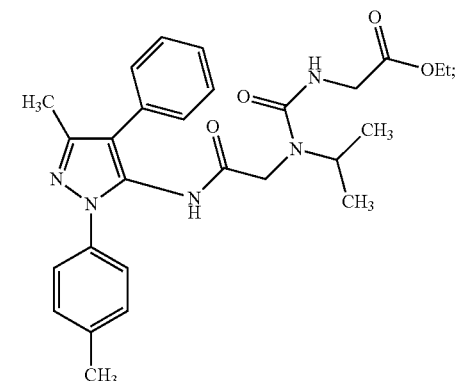
(XI)
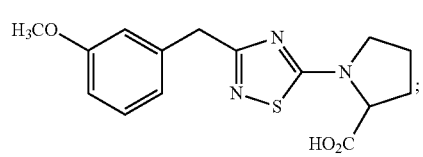
(XII)
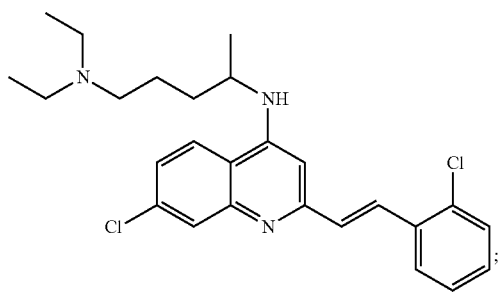
(XIII)
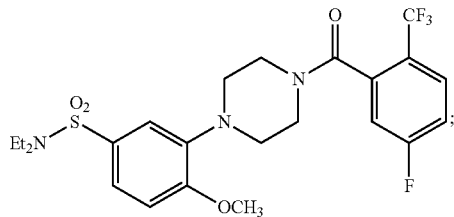
(XIV)
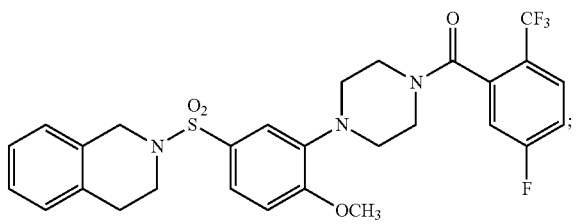
(XV)
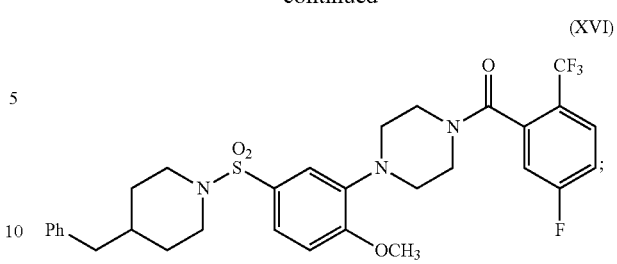
(XVI)
(XVII)
(XVIII)
and
(XIX)
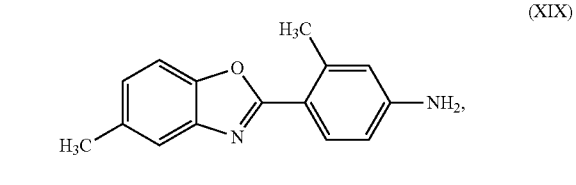
or a pharmaceutically acceptable salt thereof.
* * * * *

UNITED STATES PATENT AND TRADEMARK OFFICE
CERTIFICATE OF CORRECTION

PATENT NO.        : 8,901,129 B2                                    Page 1 of 1
APPLICATION NO.   : 13/514906
DATED             : December 2, 2014
INVENTOR(S)       : Mart Saarma et al.

It is certified that error appears in the above-identified patent and that said Letters Patent is hereby corrected as shown below:

In the Claims:

At Column 35, line 27, claim 1, below Chemical Formula (VI), insert both formula -- 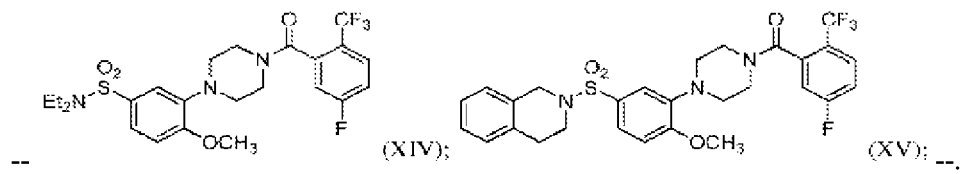 --.

Signed and Sealed this
First Day of March, 2016

Michelle K. Lee
*Director of the United States Patent and Trademark Office*